United States Patent
Norddahl et al.

(10) Patent No.: US 10,844,226 B2
(45) Date of Patent: Nov. 24, 2020

(54) METHODS FOR OBTAINING NATURAL COLOURANTS FROM PLANT BASED MATERIALS

(71) Applicant: Syddansk Universitet, Odense M (DK)

(72) Inventors: Birgir Norddahl, Ringe (DK); Behnaz Razi Parjikolaei, Herning (DK)

(73) Assignee: Syddansk Universitet, Odense (DK)

( * ) Notice: Subject to any disclaimer, the term of this patent is extended or adjusted under 35 U.S.C. 154(b) by 0 days.

(21) Appl. No.: 16/491,517

(22) PCT Filed: Mar. 7, 2018

(86) PCT No.: PCT/EP2018/055549
§ 371 (c)(1),
(2) Date: Sep. 5, 2019

(87) PCT Pub. No.: WO2018/162526
PCT Pub. Date: Sep. 13, 2018

(65) Prior Publication Data
US 2020/0017690 A1    Jan. 16, 2020

(30) Foreign Application Priority Data
Mar. 7, 2017    (EP) .................................. 17159604

(51) Int. Cl.
*C09B 61/00*    (2006.01)
*C09B 67/54*    (2006.01)
(Continued)

(52) U.S. Cl.
CPC ........ *C09B 67/0096* (2013.01); *B01D 61/027* (2013.01); *B01D 61/145* (2013.01);
(Continued)

(58) Field of Classification Search
CPC ... C09B 67/0096; C09B 61/00; B01D 61/027; B01D 61/14; B01D 61/58; B01D 61/145;
(Continued)

(56) References Cited

U.S. PATENT DOCUMENTS 4,409,254 A * 10/1983 Garin .................. C09B 67/0096
                                                                 426/250
6,620,452 B1    9/2003  Haddad et al.
(Continued)

FOREIGN PATENT DOCUMENTS

EP    0096481 B1    11/1987
EP    1967078 A1    9/2008
(Continued)

OTHER PUBLICATIONS

"Abstract of WO2010/073757A1", Database WPI, Week 201047, Thompson Scientific, London, GB, (Jul. 1, 2010), 3 pgs.
(Continued)

*Primary Examiner* — Eisa B Elhilo
(74) *Attorney, Agent, or Firm* — Schwegman Lundberg & Woessner, P.A.

(57) ABSTRACT

The present invention relates to methods for obtaining natural colorants from materials of plant origin. The method comprises a mixing step, a co-pigmentation step, an enzymatic hydrolysis step and various filtration steps carried out under specific conditions.

15 Claims, 17 Drawing Sheets

(51) Int. Cl.
*B01D 61/02* (2006.01)
*B01D 61/14* (2006.01)
*B01D 61/58* (2006.01)
*B01D 69/02* (2006.01)
*C12P 19/14* (2006.01)

(52) U.S. Cl.
CPC .............. *B01D 61/58* (2013.01); *B01D 69/02* (2013.01); *C09B 61/00* (2013.01); *C12P 19/14* (2013.01); *B01D 2315/16* (2013.01); *B01D 2317/025* (2013.01); *B01D 2317/08* (2013.01); *B01D 2325/20* (2013.01)

(58) Field of Classification Search
CPC .......... B01D 2317/025; B01D 2325/20; B01D 2317/08
See application file for complete search history.

(56) References Cited

U.S. PATENT DOCUMENTS

| | | | |
|---|---|---|---|
| 7,306,669 B1 * | 12/2007 | Zhang | A61Q 1/02 106/493 |
| 2013/0309355 A1 | 11/2013 | Wong et al. | |

FOREIGN PATENT DOCUMENTS

| | | |
|---|---|---|
| EP | 2526785 A1 | 11/2012 |
| JP | 5591122 B2 | 8/2014 |
| WO | WO-03037096 A1 | 5/2003 |
| WO | WO-2006113700 A1 | 10/2006 |
| WO | WO-2009076776 A1 | 6/2009 |
| WO | WO-2010073757 A1 | 7/2010 |

OTHER PUBLICATIONS

Galanakis, Charis M, et al., "Recovery and fractionation of different phenolic classes from winery sludge using ultrafiltration", Separation and Purification Technology, Elsevier Science, Amsterdam, NL, vol. 107, (Jan. 31, 2013), 245-251.

Mirsaeedghazi, Hossein, et al., "Comparison between Ultrafiltration and Microfiltration in the Clarification of Pomegranate Juice", Journal of Food Process Engineering, vol. 35, No. 3, (Jun. 25, 2010), 424-436.

Sari, Puspita, et al., "Colour properties, stability, and free radical scavenging activity of jambolan (Syzygium cumini) fruit anthocyanins in a beverage model system: Natural and copigmented anthocyanins", Food Chemistry, vol. 132, No. 4, (2012), 1908-1914.

Weber, Fabian, et al., "Influence of copigmentation on the stability of spray dried anthocyanins from blackberry", LWT Food Science and Technology, Academic Press, UK, vol. 75, (Aug. 21, 2016), 72-77.

* cited by examiner

METHODS FOR OBTAINING NATURAL COLOURANTS FROM PLANT BASED MATERIALS

This application is a U.S. National Stage Filing under 35 U.S.C. 371 from International Application No. PCT/EP2018/055549, filed on Mar. 7, 2018, and published as WO 2018/162526 A1 on Sep. 13, 2018, which claims the benefit of priority to European Patent Application No. 17159604.2 filed on Mar. 7, 2017, each of which is incorporated by reference herein in its entirety.

TECHNICAL FIELD OF THE INVENTION

The present invention relates to methods for obtaining natural colorants from materials of plant origin. The method comprises a mixing step, a co-pigmentation step, an enzymatic hydrolysis step and various filtration steps carried out under specific conditions.

BACKGROUND OF THE INVENTION

Juice from berries is typically produced through a process where the berries are crushed, enzymatically treated to break down pectin and ligno-cellulosic structures in the skin of the berries to enable release of juice and for the purpose of clarification and subsequently squeezing to release the juice from the berry skin or pomace.

Polyphenols in the skin of berries are known to have various beneficial uses as food supplements, natural colours, anti-oxidants, co-pigments and for treatment of cardiovascular diseases.

Polyphenols are often bound to the cell wall in leaves and berries of the plant in such a way that traditional extraction methods, which may comprise an acidic, hydrous solution or alcoholic solution, will only release a fraction of the polyphenols. Using enzymes leads to hydrolysis of the pectin in the cell wall and consequently more polyphenols are released and the yield of the extraction is multiplied.

During the last decades, consumers have developed an increasing preference for natural colorants compared to synthetic colorants. A big contributing factor to this development has been a series of research projects connecting the ingestion of synthetic colorants with a negative impact on human health. In addition, many synthetic colorants have been banned from food products during the 20th century. This leaves the food industry with little choice but to use natural colorants when it is necessary to obtain a certain colour in processed food products.

Purified anthocyanins are used as a natural colorant in the food industry and hence the anthocyanin content of e.g. berry pomace may represent a valuable raw material for the production of such natural colorants.

The presence of certain co-pigmentation compounds in the extraction process have shown to increase anthocyanin stability through the formation of complexes. This phenomenon, in which pigments and other non-coloured organic components form molecular associations or complexes, is known as co-pigmentation and often results in a colour enhancement. Co-pigmentation of anthocyanins has been shown to occur by formation of intra- or intermolecular complexes. The ability of anthocyanins to form intramolecular complexes depends on the presence of phenolic acid residues covalently bonded to the sugar moieties of the anthocyanins and by formation of pyranoanthocyanins.

It is known that the use of pectinolytic enzymes (pectinases) is inhibited by the product of the hydrolysis such as galacturonic acid and that cellulolytic enzymes (cellulases) are inhibited by the formation of glucose resulting from hydrolysis of cellulose.

However, the use of a membrane coupled to the bioreactor where the hydrolysis takes place separates small molecules like hexoses, pentose and galacturonic acid from the reactor broth by passing through the membrane, reducing their concentration in the reactor, and thus decreasing their inhibiting effect on the enzyme.

These membrane bioreactors with enzymes (e-MBR) are mainly used for clarification of juice for drinking, where a larger part of the vitamins and other juice components are contained in the produced juice compared to juice produced using conventional methods. Whereas the general designing of e-MBR's has been reported since the eighties no disclosures have been made regarding the use of e-MBR's for release of e.g. natural colorants, such as anthocyanins with anti-oxidative properties, from berry pomace with regard to utilisation of the anti-oxidants for e.g. nutraceutical purposes.

Another important advantage of using a membrane bioreactor is that by choice of membrane any spores of fungus, bacteria and virus can be excluded from the permeate, which thereby is effectively sterilised in the process. Most ultra-filtration membranes will enable this sterilising process.

WO03037096 discloses a method of extracting biologically active compounds (e.g. phenolics) from botanical material (*E. purpurea*, purple coneflower) said method including the step of mixing the botanical material and a solution including at least one acid (ascorbic acid, cinnamic acid) and at least one antioxidant (citric acid) to form a mixture. The extraction method results in an increased level of the phenolics; caftaric acid and chichoric acid in the resulting extract compared to extraction treatment with water alone.

EP2526785 discloses a process for extraction and concentration of polyphenolic compounds contained in e.g. pomaces (olives) involving e.g. the steps of: milling (the olives), subjecting the obtained mixture/liquid to enzymatic pre-treatment, followed by various filtration/purification steps, and acidification and enzymatic treatment steps (with food-grade enzymes produced in *Aspergillus niger* and *Trichoderma longibrachiatum*, such as cellulolytic and pectolytic enzymes.

WO06113700 discloses a process for preparing a concentrated polyphenolic product (antioxidants), from e.g. grape materials, the process comprising e.g. the steps of: extracting substantially all polyphenolics and non-flavonoids (resveratrol and gallic acid)) contained in grape material with a solvent (water and ethanol) followed by the removal of the solvent from the liquid polyphenolic extract to form a liquid polyphenolic concentrate. WO06113700 also discloses that the resulting liquid polyphenolic extract can be filtered through membrane plate and frame filters to remove undissolved solid material.

EP096481 discloses a method for the production of a red coloring material from anthocyanin-containing vegetable source material (e.g. pomace derived from red grapes) where said anthocyanins are extracted with sulphur dioxide, the resulting anthocyanin-extract is further treated enzymatically with pectinases and amylases and sulphuric acid is added to the resulting mixture in order to prevent co-pigment formation between anthocyanins and other flavonoids, proteins, etc.

US2013309355 discloses a method for producing purified purple sweet potato (PSP) concentrate rich in natural anthocyanin and phenolic compounds, the method comprising the phases of washing and sterilizing PSPs; grinding and blending the sterilized PSPs; adding citric acid to fix the color of PSP puree; enzymatic treatment including heating and pH adjusting the liquefied PSP slurry. Hereafter, the PSP slurry is further processed by e.g. filtration by use of membrane filtration and nano-filtering. In US2013309355 the addition of citric acid is used to fixate the color of the PSP extract.

U.S. Pat. No. 6,620,452 discloses a process for extracting plant phenolics (gallic acid) from fruits or vegetables, the process comprising inter alia the steps of: extracting macerated fruit or vegetable particles with water to yield an aqueous extract; heating the aqueous extract; adding pectinase enzyme to the extract and treating the extract with the pectinase enzyme until substantially all pectin has been removed; re-heating the extract to deactivate the remaining pectinase enzyme. Hereafter, the extracts are further processed by e.g. adding solid polyvinylpolypyrrolidone (PVPP) adsorbent to the extract.

WO09076776 discloses a process for extracting phenolic compounds from apples, comprising: (i) obtaining a sample of apple peels, (ii) extracting the peels with a food-grade solvent under conditions to extract the apple phenolic compounds into the solvent; and (iii) removing solids from the resulting extract of to provide a stock solution of apple phenolic compounds. WO09076776 further mentions that the extracting of the peels can be carried out with a mixture of acetone, water and acetic acid (to remove proanthocyanidins). No specific temperatures are indicated for the extraction process. WO09076776 contains no disclosure of a co-pigmentation step or an enzymatic hydrolysis step.

Advantages Over Prior Art

The method according to the present invention, seen as a whole, is a low energy way of extracting, purifying, and concentrating natural colorants, such as anthocyanins with anti-oxidative properties, from plant-derived material, such as berry pomace, while at the same time combining with co-pigment, such as one or more hydroxycinnamic acids, that will affect conserving the purified colorants and the anti-oxidants contained therein.

The present invention has the further advantage that the temperatures involved in the process of obtaining the natural colorants, such as anthocyanins with anti-oxidative properties, from e.g. berry-derived pomace is much lower that normally required obtaining a quantitative separation of natural colorants, such as anthocyanins with anti-oxidative properties, by conventional extraction methods.

In conventional extraction methods, the first step would normally be extraction by means of hot water, acidic solutions or alcoholic solutions at a temperature of above 65C.° and further the raw materials for the process would often be heat sterilised before the start of the operations, which again will expose the anthocyanins for elevated temperatures.

In the method according to the present invention, the temperature in the extraction stage does not exceed 50° C. and no other solvent except water is needed. The use of a membrane bioreactor with an appropriately tight filter (mesh size) will ensure a proper sterilisation of the product from which the anthocyanins are extracted without the need for elevating the temperature. These gentle operations according to the method of the present invention help e.g. preserving the antioxidants from deterioration due to high temperatures. Anthocyanins are rapidly degraded at elevated temperatures. Thus, the currently widely applied thermal extraction and concentration processes are not optimal for concentrating and extracting the anthocyanin extracts from plant materials.

Further, the process of co-pigmentation according to the method of the present invention during the extraction step, where co-pigment, such as one or more hydroxycinnamic acid(s)), are reacted with the natural colorants, such as anthocyanins with anti-oxidative properties, to form co-pigmentation complexes will e.g. increase the colour stability of the natural colorants as well as the stability of the antioxidants contained therein.

Still another advantage of the method according to the present invention is that the co-pigmented anthocyanin-complexes have an organic weight which is so much higher than that of sugars released in the bioreactor process thereby enhancing the separation process by means of an nanofiltration (NF) membrane operation subsequent to the e-MBR operation, which with a proper choice of NF membranes will retain the co-pigmented complexes and let the sugars pass with the permeate.

An further advantage of the method according to the present invention is the fact that the number of unit operations are lower than in a traditional methods of extracting, purifying and concentrating natural colourants from plant-derived material, e.g. berry pomace.

An still further advantage of the method according to the present invention is the fact that the final product obtained by the method of the present invention is a cheaper and requires less and more gentle operations compared to the methods of the prior art.

It is a well-known problem in the art that the polyphenols contained in e.g. berry pomace have been shown to degrade when released from the cell walls during traditionally applied extraction processes and ensuing time.

To overcome that problem an extraction process has been developed by the inventors, where the natural colorants, such as anthocyanins with anti-oxidative properties, are bound to co-pigments, such as one or more hydroxycinnamic acid(s), which stabilises the natural colorants, such as anthocyanins with anti-oxidative properties, and even increases their anti-oxidant and colouring capacity.

Even further, the presence of certain enzymatic compounds in the extraction process and the application of specifically defined filtration processes under well-defined reaction conditions have shown to increase anthocyanin stability through the formation of complexes.

Hence, an improved method for obtaining natural colorants, such as anthocyanins with anti-oxidative properties, from materials of plant origin would be advantageous, and in particular a more efficient, reliable, simple, yet effective method for separating the colorant product obtainable by the method according to the present invention involves e.g. the steps of: co-pigmentation of natural colorants, such as anthocyanins with anti-oxidative properties, by including only two and in a few cases three unit operations for the separation of the natural colorants from the plant moiety to which it is bound and two unit operations for concentrating the purified natural colorants, such as anthocyanins with anti-oxidative properties, and furthermore include only a few solutes (only water and a citric acid buffer) to the extract solution in addition to the enzymes used for disintegrating the plant tissue in order to release the natural colorants, such as anthocyanins with anti-oxidative properties.

Still another problem or disadvantage of the prior art methods is the use of mixtures of organic acids to enhance the extraction process, which will increase the amount of chemicals to be separated from the final product as well as increasing the price of the product (WO03037096). In the method of the present invention, this process step has been simplified by using only water and a citric acid buffer, with considerably lower amount of solvents in the extracting liquid.

In contrast to the prior art method described in e.g. EP096481, the method according to the present invention makes use of only two filtration steps for separating the natural colorants, such as anthocyanins with anti-oxidative properties, from the plant moiety they are embedded in. Moreover, the present inventors have applied co-pigments, such as one or more hydroxycinnamic acid(s), in order to make the final colorant product with a higher anti-oxidant and coloring capacity and durability and avoid the price-raising feature of adding e.g. sulfuric acid to the extraction step.

Another problem of the prior art is the use of high temperatures in the extraction process (typically above 90° C. as in WO06113700 and U.S. Pat. No. 6,620,452), which will invariably lead to destruction of a majority of the desired colorant products and thus a smaller yield, whereas the method of the present invention can perform the extraction step at less than 50° C., which combined with the co-pigmentation will increase the yield of the process.

The method according to the present invention solves the above-mentioned problems.

SUMMARY OF THE INVENTION

Natural colorants with antioxidative properties are attractive to e.g. the food industry since they combine coloring properties with potential nutrition and therapeutic effects.

Pomace, a waste product/by-product from the production of e.g. juice, is an attractive raw material for the production of e.g. anthocyanin food colorants.

Thus, an object of the present invention relates to a method of obtaining natural colorants, such as anthocyanins with anti-oxidative properties, from materials of plant origin comprising a mixing step, a co-pigmentation step, an enzymatic hydrolysis step and a nanofiltration/diafiltration step carried out at low pH at or below 3 and at relatively low temperature at or below 50° C.

Thus, one preferred aspect of the invention relates to a method for obtaining natural colorants from materials of plant origin, comprising the following steps:
(a) adding pomace from said materials of plant origin and a aqueous buffer solution into a mixing device
(b) mixing said pomace from said materials and aqueous buffer solution, followed by
(c) blending the mixed pomace obtained in step (b) in a blending device thereby obtaining a comminute homogenized slurry, followed by
(d) adding one or more hydroxycinnamic acid(s) into the slurry obtained in step (c), and
(e) adding one or more one or more hydrolytic enzyme(s) to the slurry of step (c) or (d), and
(f) adding one or more green solvent(s) to the slurry of step (c), (d) or (e)
(g) subjecting the resulting mixture obtained in step (f) to ultrafiltration in a ultrafiltration unit thereby obtaining a permeate rich in natural colorants
wherein the pH in all steps (a)-(g) is kept at or below 3 and wherein the temperature in all steps (a)-(g) is kept at or below 50° C.

Figure 1:
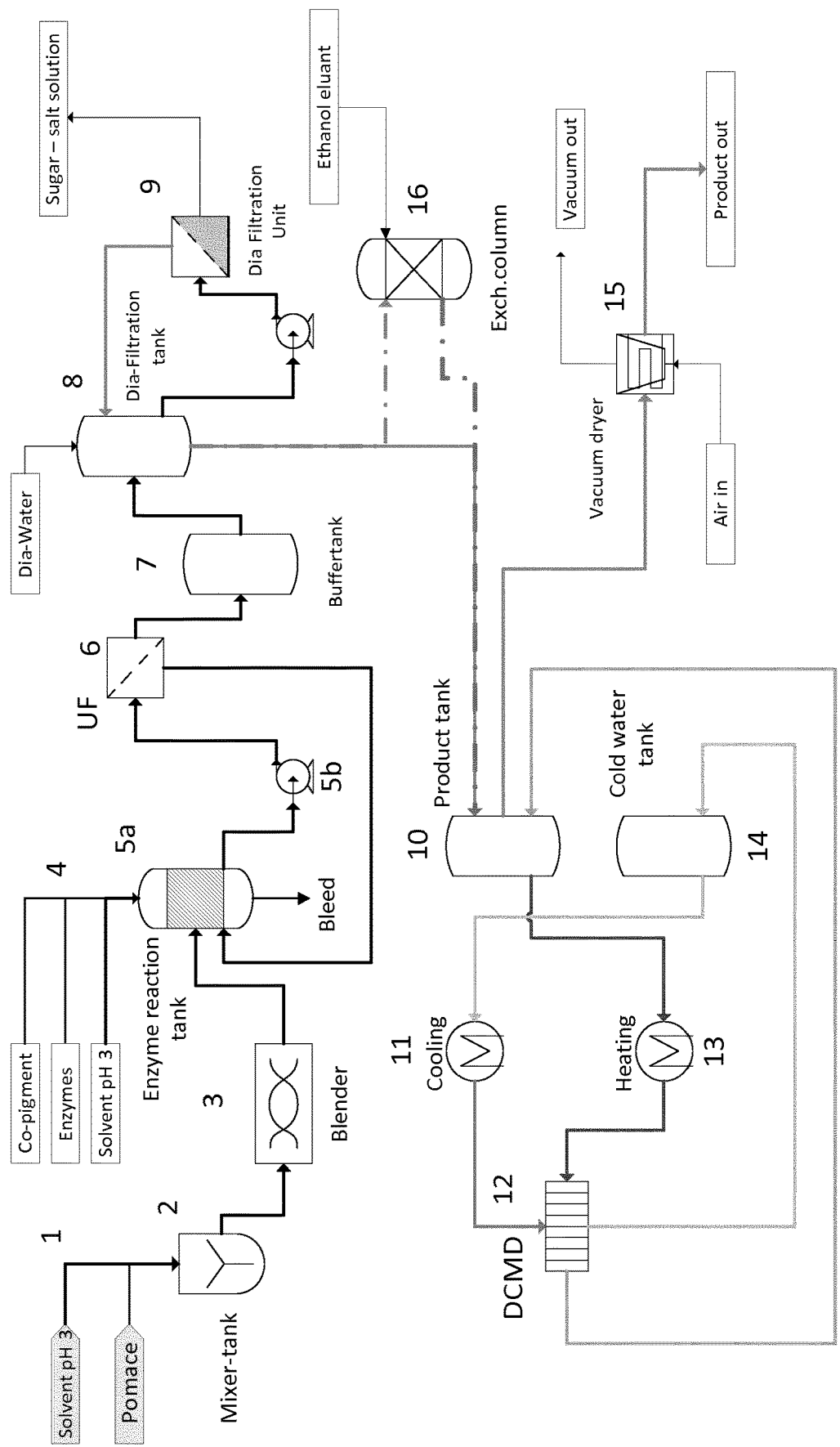
FIG. 1 shows a simplified diagram representation of the integrated process from raw materials to the final product comprising: 1. Feed lines for raw materials: Raw pomace from berry production and a buffer solution (named: solvent pH 3) consisting of citric acid and dihydrogen phosphate dissolved in dem. water buffered to pH 3. 2. A stirred tank for mixing pomace in a batch operation with buffer solution (named: Mixer-tank). 3. A pulping blender downsizing pomace in a batch process and mixing with solvent and co-pigments. 4. Feed lines for materials to the Enzyme membrane reactor: Blended raw pomace from the pulping blender, additional solvent buffered to pH 3, co-pigment agent and enzymes for the enzymatic reaction. 5a. Enzyme reaction tank where the feed mixture is reacted with the added enzymes to hydrolyse skin tissue in order to release bound anti-oxidants. This reaction is continuous with the reaction tank acting as a production buffer tank, which is processing in a fed-batch operation. This operation is temporarily stopped in order to discharge a bleed, which is a non-hydrolysable pomace component comprising mainly lignin moieties. 5b. A high pressure pump for the subsequent ultra-filtration (UF). 6. An ultra-filter (UF) separating unreacted pomace and enzymes from reaction products comprising pectin monomers, sugars, dissolved salts, solvent and anti-oxidants released form the down-graded skin tissue of the pomace. 7. Buffer tank receiving permeate from UF containing a solution of salts, sugars, pectin monomers and anti-oxidants. 8. Dia-filtration tank, where dem. water from external source is mixed with product from operation 6. (UF unit) to aid separation of anti-oxidants from solutes of smaller molecular size than anti-oxidants in unit 9. 9. Dia-filtration nano filter (NF) with an MMWCO (Mean Molecular Weight Cut-Off) of between 400 and 1000 Da, where dissolved salts, sugars, and pectin monomers are separated from anti-oxidants, which are retained by the NF due to size exclusion. This operation is a batch operation, which is terminated when the concentration of salts, sugars and pectin monomers are below a pre-set value complying with the requirements for pure anti-oxidant products. 10. Collector tank for anti-oxidants and solvent separated in the dia-fitration NF unit. 11. Cooling unit in Direct Contact Membrane Distillation (DCMD) unit cooling water receiving and condensing water vapour from the anti-oxidant product solution. 12. DCMD unit, where water from the anti-oxidant product solution is distilled off from the heated anti-oxidant product solution due to vapour pressure differences in a hydrophobic capillary membrane between the warm (45° C.) product solution and the cold receiving stream (2° C.) on the other side of the capillary membrane. 13. A heat exchanger where the anti-oxidant product solution is heated up to 45° C. The final concentrated solution (~65° brix) is collected in the product tank (10). 14. Cold water tank for the receiving condensed water vapour stream in the DCMD unit. 15. A vacuum dryer where residual water from the anti-oxidant product solution is removed in order to achieve a dry powder consisting of anti-oxidants. 16. An auxiliary chromatographic exchange column, packed with an affinity chromatographic matrix with a high affinity for polyphenol and/or natural colorants, such as anthocyanins with anti-oxidative properties, which is necessary in case the dia-filtration NF unit is insufficient in separating polyphenol and/or natural colorants, such as anthocyanins with anti-oxidative properties from sugar and salt solution moieties. The exchange column unit comprises the column and a distilliation unit for recovery of the ethanol eluant.
Figure 2:
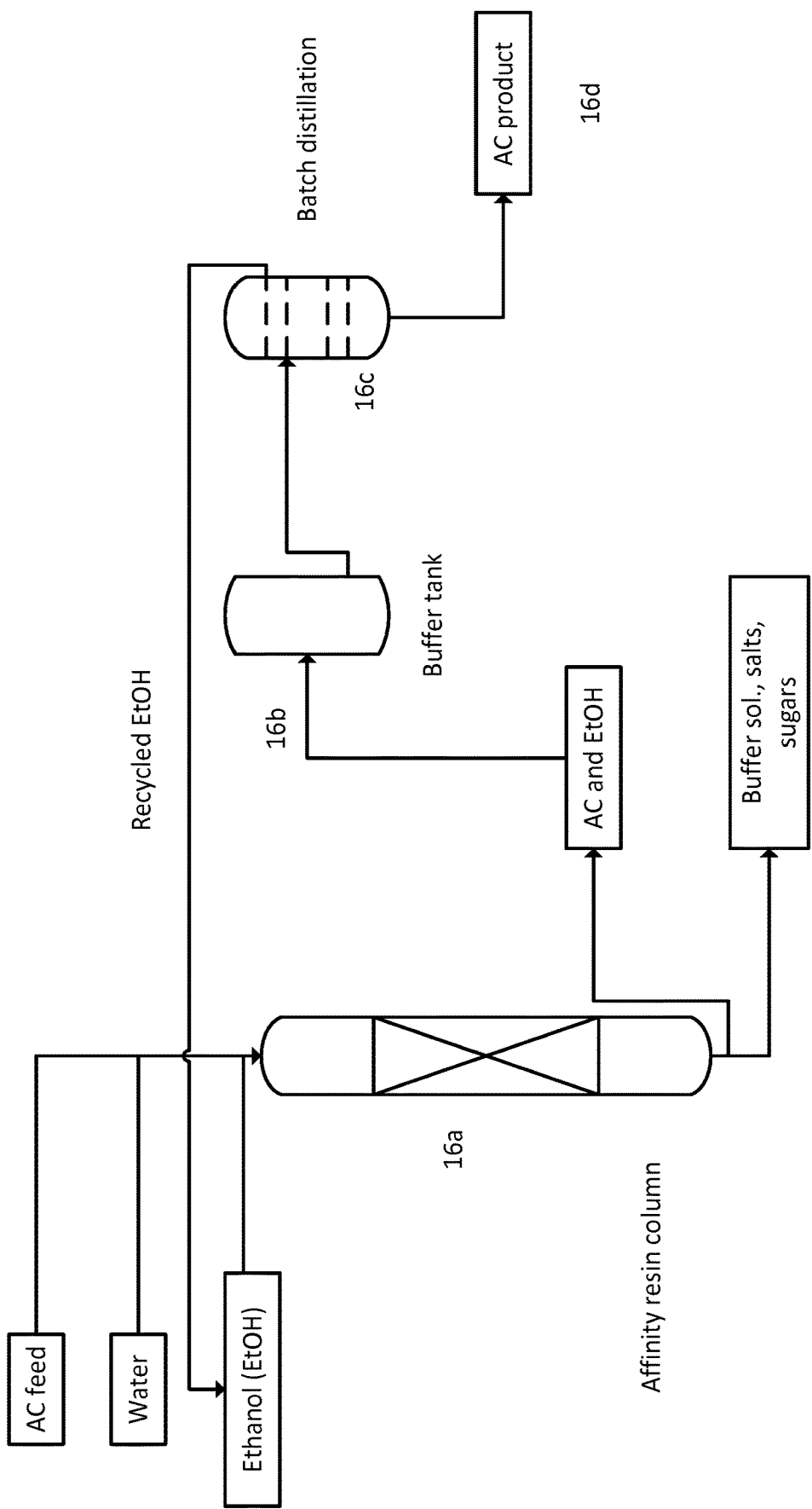
FIG. 2 (affinity chromatographic process with eluant recovery) shows a detailed diagram of the method of the present invention including the final chromatography steps for concentrating and purifying the resulting colorant-rich retentate. 16a. An affinity chromatographic column filled with an appropriate resin, which specifically binds anti-oxidants and anti-oxidant co-pigment compounds. The column is applied with the retentate from the NF diafiltration containing anti-oxidants and remaining buffer solvent, salts and sugars. In the column 16a only the anti-oxidants are retained. The other components are eluted with the water eluent moving phase, which constitutes the separation operation purifying the anti-oxidant moiety. Subsequently the anti-oxidant moiety is eluted with ethanol (EtOH) and collected in the receiving buffer tank 16b. The solution of anti-oxidants and EtOH is subsequently separated in a batch distillation unit 16c and the EtOH, which comprises the light fraction is recycled to the column 16a for further use as an eluent. The product 16d is then pumped to the vacuum drying unit (15) for dewatering and drying.

The present invention will now be described in more detail in the following.

DETAILED DESCRIPTION OF THE INVENTION

Definitions

Prior to discussing the present invention in further details, the following terms and conventions will first be defined:

Anthocyanin

According to the present invention, anthocyanin refers to a common description of the glycosides of anthocyanidins. All anthocyanidins consist of a three ringed structure (2-phenyl-benzopyrylium). Anthocyanins are water-soluble vacuolar pigments that may appear red, purple, or blue depending on the pH. They belong to a parent class of molecules called flavonoids synthesized via the phenylpropanoid pathway. Anthocyanins occur in all tissues of higher plants, including leaves, stems, roots, flowers, and fruits. Anthocyanins occur in all tissues of higher plants, including leaves, stems, roots, flowers, and fruits.

Blending (in Blending or Size Reduction Device)

According to the present invention, blending refers to a process in which a mixture of liquids and particles are reduced in size with regard to the particles in the mixture forming a suspension with particles with an average size of no more than 100 μm and a maximum size of no more than 500 μm. Equipment used for this process are characterised as fine and ultra fine size reduction or communition equipment.

Co-Pigmentation (of Anthocyanins)

According to the present invention, co-pigmentation refers to a widespread phenomenon in nature and can occur in fruit- and berry derived products such as juices and wines. Moreover, this phenomenon can enhance the color and stability of fruit and berry products, for example, in purees, jams, and syrups. In food science, co-pigmentation is considered an important interaction, as color is one of the quality factors that affects consumer acceptance of food and the anthocyanins color stability is still an issue in the industry. There are several mechanisms describing the co-pigmentation phenomenon. The most crucial mechanisms, called intermolecular co-pigmentation (non-covalent reaction between colored anthocyanins and colorless co-pigments, such as flavonoids, polyphenols, amino acids and anthocyanins themselves) and intramolecular co-pigmentation (covalent acylation of the anthocyanin molecule, which can stabilize the pigments), were introduced to illustrate the increased stability of acylated anthocyanins. Copigmentation involves two main effects that can be easily detected: hyperchromic effect and bathochromic shift. The hyperchromic effect is an increase of the absorption intensity at the maximum wavelength. The bathochromic shift is the one towards a higher wavelength of the absorption spectrum. Co-pigmentation is affected by several factors, while pH is an important factor, it has been discovered that the co-pigment effect occurs from pH values close to 1 to 7. Other factors that may affect the co-pigmention phenomenon are the type of anthocyanins and co-pigments present, the concentration of anthocayanins and co-pigments and temperature. In accordance with the present invention, polyphenols like anthocyanins released by the enzymatic action react with the added hydroxycinnamic acid(s) forming co-pigments. The co-pigmentation step has been shown by the inventors to reduce the product inhibition of the hydrolysing enzymes and thus increase the efficiency of the enzymatic hydrolysation process.

Diafiltration

As the concentrations of solutes in the permeate seldom exceeds the concentration in the retentate and are normally smaller, even only slightly retained solutes will be concentrated on the retentate side. When the retentate is increasingly concentrated the flux across the membrane often decreases due to build up of osmotic pressure, fouling, scaling, increasing viscosity and/or concentration polarization at the membrane surface. If the desired separation has not yet occurred when the permeate flux decrease to unfeasible levels, the flux may be improved by reducing the feed concentration again by addition of water. This process is known as diafiltration.

Dry Matter Content

In accordance to the present invention dry matter content refers to the dry matter contents of solid fractions, which may contain pomace and filter cakes. Also, dry matter content refers to the dry matter content of liquid fractions which may contain filtrate, retentate and permeate.

Enzymatic Hydrolysis

In the method according to the present invention, a membrane bioreactor is used in which e.g. berry pomace is mixed with a buffer solution at an optimum extraction conditions regarding the pH of the buffer solution, pomace to buffer ratios, natural phenolic acids like ferulic acid concentration and subsequently different enzymes e.g. pectinases, cellulases and hemi-cellulases at a temperature and concentration most favourable for the enzymatic hydrolysis of the berry skin walls. Plant cell walls are hydrolysed and degraded by the action of the enzymes, which will release the colorant (polyphenols) bonded to the cell walls. In addition, using membrane technology, the product of the hydrolysis (sugars, antioxidants, and galacturonic acid) as well as co-pigments in the fermenter will be separated as a fraction called permeate which in turn results in further reduction of the inhibitory effect of the product on the hydrolysing enzymes.

Enzyme Reaction Tank

According to the present invention, enzyme reaction tank refers to a vessel or tank in which the mixture of blended pomace in a liquid buffer suspension and enzymes are agitated in order to achieve a uniform contact between enzymes and the tissue of the pomace to obtain the best possible hydrolyzation by the enzymatic process. The enzyme reaction tank is connected to an ultra filter that retains not reacted tissue material and enzymes.

Green Solvent

According to the present invention, green solvent refer to environmentally friendly solvents or biosolvents, which are derived from the processing of agricultural crops. Processing agricultural crops is processes that uses 1. generation crops (i.e. crops also grown for food) and 2. generation crops (i.e. biomass, which is waste after the edible crop has been harvested i.e. corn stalks, straw from grain crops etc. as raw material). The processing concerns heat treatment with water to solubilise lignin, which is encrusting cellulose and hemicellulose enabling a subsequent fermentation of said cellulose and hemicellulose to organic acids like lactic acid, acidic acid, citric acid that form basis for production of green solvents. Fermentation is performed with bacteria and fungi normally used for food processing, i.e. GRAS (Generally Recognized As Safe) agents. Ethyl lactate, for example whose structure is shown below, is a green solvent derived from processing of e.g. corn. Other non-limiting examples of green solvents are water and simple alcohols such as ethanol and methanol. Green solvents are solvents made from biomass and inorganic salts normally considered safe in food i.e. phosphorous salts like $NaH_2PO_4$ and $Na_2HPO_4$ used as salts in pH buffer, citric acid alone and in combination with hydrogen phosphates, acetic acid, malonic acid, lactic acid, succinic acid, glycerol and choline are typical examples of solvents, that alone, dissolved in water or mixed in different ratios are considered safe to use from both an environmental and a health aspect. Whereas traditional solvents are often toxic or are chlorinated, green solvents, on the other hand, are generally derived from renewable resources and biodegrade to innocuous, often naturally occurring product Hydroxycinnamic Acid(s) (Co-Pigment)

According to the present invention, hydroxycinnamic acids (hydroxycinnamates) refer to a class of aromatic acids or phenylpropanoids having a $C_6$-$C_3$ skeleton. These compounds are hydroxy derivatives of cinnamic acid. Co-pigment refers to naturally occurring molecules in plants that do not significantly contribute to the color. Hydroxycinnamic acid(s) represents such co-pigments. In the synthesis of hydroxycinnamic acids, phenylalanine is first converted to cinnamic acid by the action of the enzyme phenylalanine ammonia-lyase (PAL). A series of enzymatic hydroxylations and methylations leads to e.g. coumaric acid, caffeic acid, ferulic acid, 5-hydroxyferulic acid, and sinapic acid. Co-pigments in general are composed of a wide range of different molecules, such as flavonoids and other polyphenols, alkaloids, amino acid, organic acid and the anthocyanins themselves. Hydroxycinnamic acid(s) are a class of aromatic acids or phenylpropanoids having a $C_6$-$C_3$ skeleton. These compounds are hydroxy derivatives of cinnamic acid. In the category of phytochemicals that can be found in food, there are: α-Cyano-4-hydroxycinnamic acid, caffeic acid, cichoric acid, cinnamic acid, chlorogenic acid, diferulic acids, coumaric acid, coumarin, ferulic acid (3-methoxy-4-hydroxycinnamic acid), sinapinic acid (3,5-dimethoxy-4-hydroxycinnamic acid or sinapic acid).

Fermentor

According to the present invention, fermentor refers to a vessel in which a fermentation process (microbial conversion of substrates into various products i.e. alcohols, acids or gas) takes place.

Flux

According to the present invention, flux refers to the productivity of membrane and typically expressed as volume per area per unit of time, defined as equation of:

$$J = \frac{V}{A \Delta t};$$

where J is the permeate flux, A is the membrane area ($m^2$), and V is the permeate volume (Litre) collected in time interval of $\Delta t$ (hour). The unit commonly used is LMH.

Homogenized Slurry (of Comminuted Pomace)

According to the present invention, homogenized slurry (e.g. of comminuted, size reduced pomace) refers to a slurry having an average fiber size between 100 microns and 500 microns.

Maceration

Maceration refers to the process of macerating, i.e. to soften by soaking or diminution to smaller particles.

Mixing (in Mixing Device)

According to the present invention, mixing refers to agitation in a storage tank before the blending/size reduction operation, where the best possible contact between the buffer solution and the pomace is achieved.

Membrane Bioreactors with Enzymes (e-MBR, EMBS's)

Membrane bioreactor (MBR) is the combination of a membrane process like microfiltration or ultrafiltration with e.g. a suspended growth bioreactor. Membrane bioreactors with enzymes (e-MBR) are mainly used for clarification of juice for drinking, where a larger part of the vitamins and other juice components are contained in the produced juice compared to juice produced using conventional methods and no disclosures have been made regarding the use of e-MBR's for release of e.g. colourants and/or anti-oxidants from berry pomace. Another important feature of using a membrane bioreactor for such purposes is that by choice of membrane any spores of fungus, bacteria and virus can be excluded from the permeate, which thereby is effectively sterilised in the process.

Molecular Cut-Off (of Ultrafiltration Unit)

According to the present invention, molecular cut-off of the membrane of a ultrafiltration comprises a molecular cut-off of 20 kDa-50 kDa, such as 20 kDa-40 kDa, such as 20 kDa-30 kDa, most preferably approx. 20 kDa. As a non-limiting example, a molecular cut-off will allow particles having molecular weight of less than 20 kDa to pass the ultrafiltration membrane.

Molar Ratio

According to the present invention, molar ratio (e.g. molar ratio between ferulic acid and antocyanin) refers to the ratio between molarity of ferulic acid (e.g. weight (g) of the ferulic acid/molecular weight of ferulic acid (g/mol)) and the molarity of the anthocyanin (e.g. weight of the anthocyanin occurred in the solution (g)/average molecular weight of the anthocyanins (g/mol)).

Nanofiltration/Diafiltration

The permeate obtained in the co-pigmentation and enzymatic hydrolysis steps (in the MBR section) is subsequently subjected to treatment using a nanofiltration (NF) unit, where by action of a diafiltration process sugars and galacturonic acid as well as the sugar moities bonded to the aglycones is separated from polyphenols/aglycones. Nanofiltration is a membrane filtration-based method with a Mean Molecular Weight Cut-Off (MWCO) between 200 Da and 1000 Da (1 kDa) depending on operational conditions whichplace them between Ultra Filtration and Reverse Osmosis.

Natural Colorant

According to the present invention, natural colorant refers to water-soluble natural colorants with antioxidative properties which among other things may be attractive to e.g. the food industry since they combine coloring properties with potential nutrition and therapeutic effects.

A non-limiting example is polyphenols, such as anthocyanins with anti-oxidative properties, derived from berry pomace. Natural colorants obtained according to the present inventions comprise antioxidant-containing pigments selected from a group of water-solubles consisting of anthocyanin, polyphenols such as tannic acid, ellagitannin, catechin, phenol, flavonoid and flavonol.

Natural Materials Based on Plants (*Aronia melanocarpa*)

*Aronia melanocarpa*, sometimes also referred to as black chokeberry, has attracted scientific interest due to its deep purple, almost black pigmentation that arises from dense colorant contents of polyphenols, especially anthocyanins. The plant produces these colorant pigments mainly in the leaves and skin of the berries to protect the pulp and seeds from constant exposure to ultraviolet radiation and production of free radicals. Analysis of polyphenols in chokeberries has identified the following individual chemicals (among hundreds known to exist in the plant kingdom): cyanidin-3-galactoside, cyanidin-3-arabinoside, quercetin-3-glycoside, epicatechin, caffeic acid, delphinidin, petunidin, pelargonidin, peonidin, and malvidin. All these except caffeic acid are members of the flavonoid category of phenolics.

Nutraceuticals

According to the present invention, nutraceutical refers to a foodstuff (as a fortified food or dietary supplement) that provides health benefits in addition to its basic nutritional value. Nutraceuticals are concentrated forms of food or food constituents that can be taken in pills, powder, or other medicinal forms that have specific health benefits.

Optional Additional Steps of the Method of the Invention

In the method according to the present application, the obtained natural colorants, such as anthocyanins with anti-oxidative properties, may subsequently, when needed, be treated again in a polishing step utilising an affinity chromatographic column where the polyphenols are separated exclusively from traces of residual sugars from the nanofiltration treatment. Subsequently, still another addition of hydroxycinnamic acid(s) may be added in order to further increase the amount of co-pigment complexes thereby increasing the stabilisation of the final product, while increasing the anti-oxidant and colouring capacity of the product. Last the purified solution containing co-pigmented natural colorants, such as anthocyanins with anti-oxidative properties, are concentrated with a membrane distillation technology (MD) and finally dried in a conventional vacuum dryer.

Phenolic Acid

According to the present invention, phenolic acids or phenolcarboxylic acids refer to types of aromatic acid compound. Included in that class are substances containing a phenolic ring and an organic carboxylic acid function. Two important naturally occurring types of phenolic acids are hydroxybenzoic acids and hydroxycinnamic acids, which are derived from non-phenolic molecules of benzoic and cinnamic acid, respectively.

Polyphenols

According to the present invention, polyphenols (also known as polyhydroxyphenols) refer to a structural class of mainly natural, but also synthetic or semisynthetic, organic chemicals characterized by the presence of large multiples of phenol structural units. Examples include tannic acid and ellagitannin. The most abundant polyphenols are the condensed tannins, found in virtually all families of plants.

Pomace

According to the present invention, pomace refers a waste product/by-product from the production of e.g. juice, is an attractive raw material for the production of e.g. anthocyanin food colorants. As a non-limiting example, pomace also covers residual pomace obtained after pressing for juice production as well as dried pomace.

Storage/Buffer Tank

According to the present invention, storage or buffer tank refers to a vessel, where the product of the previous operation is stored before the subsequent operation.

Ultrafiltration

According to the present invention, ultrafiltration refers to a filtration process for obtaining a permeate essentially free from enzyme and non-hydrolysed tissues. Considering the molecular weight of sugars (Sorbitol, Fructose, and Glucose; approx. 180 g/mol), anthocyanins (Cy 3-galactoside, Cy 3-glucoside, Cy 3-arabinoside, Cy 3-xyloside; approx. 450 g/mol), and galacturonic acid (194 g/mol), these compounds will pass through the 20 KDa membrane while enzymes (bigger than 50 KDa) and pomace (240 µm) with higher particle size than 20 KDa will be rejected and recycled to the reactor. In addition, bacteria with average size of 0.2 µm will also be rejected by membrane.

The colorant-rich co-pigment mixtures obtained according to the method of the invention must pass the UF-membrane as a permeate along with components such as galactoronic acid, glucose, salt whereas enzymes and non-hydrolysed matter must be retained in the UF membrane as retentate. In one embodiment of the present invention the molecular cut-off of the ultrafiltration filter is 20 kDa-50 kDa, such as 20 kDa-40 kDa, such as 20 kDa-30 kDa, most preferably approx. 20 kDa.

In the context of the above definitions, one preferred aspect of the invention relates to a method for obtaining natural colorants from materials of plant origin, comprising the following steps:
- (a) adding pomace from said materials of plant origin and a aqueous buffer solution into a mixing device
- (b) mixing said pomace from said materials and aqueous buffer solution, followed by
- (c) blending the mixed pomace obtained in step (b) in a blending device thereby obtaining a comminute homogenized slurry, followed by
- (d) adding one or more hydroxycinnamic acid(s) into the slurry obtained in step (c), and
- (e) adding one or more one or more hydrolytic enzyme(s) to the slurry of step (c) or (d), and
- (f) adding one or more green solvent(s) to the slurry of step (c), (d) or (e)
- (g) subjecting the resulting mixture obtained in step (f) to ultrafiltration in a ultrafiltration unit thereby obtaining a permeate rich in natural colorants wherein the pH in all steps (a)-(g) is kept at or below 3 and wherein the temperature in all steps (a)-(g) is kept at or below 50° C.

Another embodiment of the present invention is to provide a method for obtaining natural colorants from materials of plant origin, comprising the following steps:
- (a) in a batch process; adding pomace from said materials of plant origin and a aqueous buffer solution into a mixing device, mixing said pomace from said materials and aqueous buffer solution, blending the mixed pomace obtained in a blending device thereby obtaining a comminute homogenized slurry, followed by
- (b) adding one or more hydroxycinnamic acid(s) into the slurry obtained in step (a), and
- (c) adding one or more one or more hydrolytic enzyme(s) to the slurry of step (a) or (b), and
- (d) adding one or more green solvent(s) to the slurry of step (a), (b) or (b)
- (e) subjecting the resulting mixture obtained in step (d) to ultrafiltration in a ultrafiltration unit thereby obtaining a permeate rich in natural colorants wherein the pH in all steps (a)-(e) is kept at or below 3 and wherein the temperature in all steps (a)-(e) is kept at or below 50° C.

Still another embodiment of the invention relates to a method for obtaining natural colorants from materials of plant origin, comprising the following steps:
- (a) adding pomace from said materials of plant origin and a aqueous buffer solution into a mixing device
- (b) mixing said pomace from said materials and aqueous buffer solution, followed by
- (c) blending the mixed pomace obtained in step (b) in a blending device thereby obtaining a comminute homogenized slurry, followed by
- (d) adding one or more hydroxycinnamic acid(s) into the slurry obtained in step (c), and
- (e) adding one or more one or more hydrolytic enzyme(s) to the slurry of step (c) or (d), and
- (f) adding one or more green solvent(s) to the slurry of step (c), (d) or (e)
- (g) subjecting the resulting mixture obtained in step (f) to ultrafiltration in a ultrafiltration unit thereby obtaining a permeate rich in natural colorants wherein steps (d)-(f) of claim 1 are carried out in a reactor vessel such as an enzyme reaction tank, a storage tank or a fermentor and wherein the pH in all steps (a)-(g) is kept at or below 3 and wherein the temperature in all steps (a)-(g) is kept at or below 50° C.

Still another embodiment of the invention relates to a method for obtaining natural colorants from materials of plant origin, comprising the following steps:
- (a) adding pomace from said materials of plant origin and a aqueous buffer solution into a mixing device
- (b) mixing said pomace from said materials and aqueous buffer solution, followed by
- (c) blending the mixed pomace obtained in step (b) in a blending device thereby obtaining a comminute homogenized slurry, followed by
- (d) transferring the comminute homogenized slurry og step (c) to a reactor vessel as a fed-batch process, followed by
- (e) adding one or more hydroxycinnamic acid(s) into the slurry obtained in step (c), and
- (f) adding one or more one or more hydrolytic enzyme(s) to the slurry of step (c) or (e), and
- (g) adding one or more green solvent(s) to the slurry of step (c), (e) or (f)
- (h) subjecting the resulting mixture obtained in step (g) to ultrafiltration in a ultrafiltration unit thereby obtaining a permeate rich in natural colorants wherein the pH in all steps (a)-(h) is kept at or below 3 and wherein the temperature in all steps (a)-(h) is kept at or below 50° C.

Still another embodiment of the invention relates to a method for obtaining natural colorants from materials of plant origin, comprising the following steps:
- (a) adding pomace from said materials of plant origin and a aqueous buffer solution into a mixing device
- (b) mixing said pomace from said materials and aqueous buffer solution, followed by
- (c) blending the mixed pomace obtained in step (b) in a blending device thereby obtaining a comminute homogenized slurry, followed by
- (d) adding one or more hydroxycinnamic acid(s) selected from a group consisting of natural phenolic acids like ferulic acid, α-cyano-4-hydroxycinnamic acid, caffeic acid, cichoric acid, cinnamic acid, chlorogenic acid, diferulic acids, coumaric acid, coumarin, ferulic acid, sinapic acid, benzoic acid and gallic acid into the slurry obtained in step (c), and
- (e) adding one or more one or more hydrolytic enzyme(s) to the slurry of step (c) or (d), and
- (f) adding one or more green solvent(s) to the slurry of step (c), (d) or (e)
- (g) subjecting the resulting mixture obtained in step (f) to ultrafiltration in a ultrafiltration unit thereby obtaining a permeate rich in natural colorants wherein the pH in all steps (a)-(g) is kept at or below 3 and wherein the temperature in all steps (a)-(g) is kept at or below 50° C.

Still another embodiment of the invention relates to a method for obtaining natural colorants from materials of plant origin, comprising the following steps:
- (a) adding pomace from said materials of plant origin and a aqueous buffer solution into a mixing device
- (b) mixing said pomace from said materials and aqueous buffer solution, followed by
- (c) blending the mixed pomace obtained in step (b) in a blending device thereby obtaining a comminute homogenized slurry, followed by (d) adding one or more hydroxycinnamic acid(s) into the slurry obtained in step (c), and
(e) adding one or more one or more hydrolytic enzyme(s) selected from a group consisting of ligninases such as lignin peroxidases, pectolytic enzymes, pectinases, glucanase, arabinose, galactanase, rhamno-galcturonase, laccases, cellulases and hemi-cellulases to the slurry of step (c) or (d), and
(f) adding one or more green solvent(s) to the slurry of step (c), (d) or (e)
(g) subjecting the resulting mixture obtained in step (f) to ultrafiltration in a ultrafiltration unit thereby obtaining a permeate rich in natural colorants wherein the pH in all steps (a)-(g) is kept at or below 3 and wherein the temperature in all steps (a)-(g) is kept at or below 50° C.

Still another embodiment of the invention relates to a method for obtaining natural colorants from materials of plant origin, comprising the following steps:
(a) adding pomace from said materials of plant origin and a aqueous buffer solution into a mixing device
(b) mixing said pomace from said materials and aqueous buffer solution, followed by
(c) blending the mixed pomace obtained in step (b) in a blending device thereby obtaining a comminute homogenized slurry, followed by
(d) adding one or more hydroxycinnamic acid(s) into the slurry obtained in step (c), and
(e) adding one or more one or more hydrolytic enzyme(s) to the slurry of step (c) or (d), and
(f) adding one or more green solvent(s) to the slurry of step (c), (d) or (e) resulting in green solvent: slurry ratio of 30-50:1 (w/w), such as 32-48:1 (w/w), such as 34-46:1 (w/w), such as 36-44:1 (w/w), such as 38-42:1 (w/w), such as 40:1 (w/w).
(g) subjecting the resulting mixture obtained in step (f) to ultrafiltration in a ultrafiltration unit thereby obtaining a permeate rich in natural colorants wherein the pH in all steps (a)-(g) is kept at or below 3 and wherein the temperature in all steps (a)-(g) is kept at or below 50° C.

Still another embodiment of the invention relates to a method for obtaining natural colorants from materials of plant origin, comprising the following steps:
(a) adding pomace from said materials of plant origin and a aqueous buffer solution into a mixing device
(b) mixing said pomace from said materials and aqueous buffer solution, followed by
(c) blending the mixed pomace obtained in step (b) in a blending device thereby obtaining a comminute homogenized slurry, followed by
(d) adding one or more hydroxycinnamic acid(s) into the slurry obtained in step (c), and
(e) adding one or more one or more hydrolytic enzyme(s) to the slurry of step (c) or (d), and
(f) adding one or more green solvent(s) to the slurry of step (c), (d) or (e)
(g) subjecting the resulting mixture obtained in step (f) to ultrafiltration in a ultrafiltration unit thereby obtaining a permeate rich in natural colorants comprising antioxidant-containing pigments selected from a water-soluble group of compounds consisting of anthocyanin, polyphenols such as tannic acid, ellagitannin, catechin, phenol, flavonoid and flavonol, wherein the pH in all steps (a)-(g) is kept at or below 3 and wherein the temperature in all steps (a)-(g) is kept at or below 50° C.

Still another embodiment of the invention relates to a method for obtaining natural colorants from materials of plant origin selected from the group consisting of plants, fruits, berries such as black berries, cherries, red currants, apple, aronia, elderberry, raspberry, strawberry, black chokeberry (*Aronia melanocarpa*), cowberry, bilberry, elderberry and black elderberry, comprising the following steps:
(a) adding pomace from said materials of plant origin and a aqueous buffer solution into a mixing device
(b) mixing said pomace from said materials and aqueous buffer solution, followed by
(c) blending the mixed pomace obtained in step (b) in a blending device thereby obtaining a comminute homogenized slurry, followed by
(d) adding one or more hydroxycinnamic acid(s) into the slurry obtained in step (c), and
(e) adding one or more one or more hydrolytic enzyme(s) to the slurry of step (c) or (d), and
(f) adding one or more green solvent(s) to the slurry of step (c), (d) or (e)
(g) subjecting the resulting mixture obtained in step (f) to ultrafiltration in a ultrafiltration unit thereby obtaining a permeate rich in natural colorants wherein the pH in all steps (a)-(g) is kept at or below 3 and wherein the temperature in all steps (a)-(g) is kept at or below 50° C.

Still another embodiment of the invention relates to a method for obtaining natural colorants from materials of plant origin, comprising the following steps:
(a) adding pomace from said materials of plant origin and a aqueous buffer solution into a mixing device in *a pomace*: buffer solution ratio of 1:20-100 w/w, such as 1:25-95 w/w, such as 1:30-90 w/w, such as 1:35-85 w/w, such as 1:35-80 w/w, such as 1:35-75 w/w, such as 1:35-70 w/w, such as 1:35-65 w/w, such as 1:40-60 w/w, such as 1:45-55 w/w, preferably 1:50 w/w, followed by
(b) mixing said pomace from said materials and aqueous buffer solution, followed by
(c) blending the mixed pomace obtained in step (b) in a blending device thereby obtaining a comminute homogenized slurry, followed by
(d) adding one or more hydroxycinnamic acid(s) into the slurry obtained in step (c), and
(e) adding one or more one or more hydrolytic enzyme(s) to the slurry of step (c) or (d), and
(f) adding one or more green solvent(s) to the slurry of step (c), (d) or (e)
(g) subjecting the resulting mixture obtained in step (f) to ultrafiltration in a ultrafiltration unit thereby obtaining a permeate rich in natural colorants wherein the pH in all steps (a)-(g) is kept at or below 3 and wherein the temperature in all steps (a)-(g) is kept at or below 50° C.

Still another embodiment of the invention relates to a method for obtaining natural colorants from materials of plant origin, comprising the following steps:
(a) adding pomace from said materials of plant origin and a aqueous buffer solution into a mixing device
(b) mixing said pomace from said materials and aqueous buffer solution, followed by
(c) blending the mixed pomace obtained in step (b) in a blending device thereby obtaining a comminute homogenized slurry, followed by
(d) adding one or more hydroxycinnamic acid(s) into the slurry obtained in step (c), and (e) adding one or more one or more hydrolytic enzyme(s) to the slurry of step (c) or (d), and (f) adding one or more green solvent(s) to the slurry of step (c), (d) or (e)

(g) subjecting the resulting mixture obtained in step (f) to ultrafiltration in a ultrafiltration unit comprising a molecular cut-off of 20 kDa-50 kDa, such as 20 kDa-40 kDa, such as 20 kDa-30 kDa, most preferably approx. 20 kDa thereby obtaining a permeate rich in natural colorants wherein the pH in all steps (a)-(g) is kept at or below 3 and wherein the temperature in all steps (a)-(g) is kept at or below 50° C.

Still another embodiment of the invention relates to a method for obtaining natural colorants from materials of plant origin, comprising the following steps:

(a) adding pomace from said materials of plant origin and a water-based buffer solution into a mixing device (b) mixing said pomace from said materials and water-based buffer solution, followed by (c) blending the mixed pomace obtained in step (b) in a blending device thereby obtaining a comminute homogenized slurry, followed by (d) adding one or more hydroxycinnamic acid(s) into the slurry obtained in step (c), and (e) adding one or more one or more hydrolytic enzyme(s) to the slurry of step (c) or (d), and (f) adding water to the slurry of step (c), (d) or (e)

(g) subjecting the resulting mixture obtained in step (f) to ultrafiltration in a ultrafiltration unit thereby obtaining a permeate rich in natural colorants wherein the pH in all steps (a)-(g) is kept at or below 3 and wherein the temperature in all steps (a)-(g) is kept at or below 50° C.

Still another embodiment of the invention relates to a method for obtaining natural colorants from materials of plant origin, comprising the following steps:

(a) adding pomace from said materials of plant origin and a aqueous buffer solution into a mixing device (b) mixing said pomace from said materials and aqueous buffer solution, followed by (c) blending the mixed pomace obtained in step (b) in a blending device thereby obtaining a comminute homogenized slurry, followed by (d) adding one or more hydroxycinnamic acid(s) into the slurry obtained in step (c), and (e) adding one or more one or more hydrolytic enzyme(s) to the slurry of step (c) or (d), and (f) adding one or more green solvent(s) to the slurry of step (c), (d) or (e)

(g) subjecting the resulting mixture obtained in step (f) to ultrafiltration in a ultrafiltration unit thereby obtaining a permeate rich in natural colorants wherein the pH in all steps (a)-(g) is kept at or below 3 and wherein the temperature in all steps (a)-(g) is kept at or below 50° C., such as between 0° C.-50° C., such as between 5° C.-50° C., such as between 10° C.-50° C., such as between 15° C.-50° C., such as between 20° C.-50° C., such as between 25° C.-50° C., such as between 30° C.-50° C., such as between 35° C.-50° C., such as between 40° C.-50° C., such as between 45° C.-50° C., such as 30° C., such as 50° C.

A most preferred embodiment of the invention relates to a method for obtaining anthocyanin from black chokeberry (*Aronia melanocarpa*), comprising the following steps:

(a) adding pomace from black chokeberry (*Aronia melanocarpa*) and a aqueous buffer solution into a mixing device (b) mixing said pomace and aqueous buffer solution, followed by (c) blending the mixed pomace obtained in step (b) in a blending device thereby obtaining a comminute homogenized slurry, followed by (d) adding ferulic acid into the slurry obtained in step (c), and (e) adding one or more pectolytic enzyme(s) to the slurry of step (c) or (d), and (f) adding one or more green solvent(s) to the slurry of step (c), (d) or (e)

(g) subjecting the resulting mixture obtained in step (f) to ultrafiltration in a ultrafiltration unit thereby obtaining a permeate rich in anthocyanin wherein the pH in all steps (a)-(g) is kept at or below 3 and wherein the temperature in all steps (a)-(g) is kept at or below 50° C.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

Examples

Example 1

Enzymatic Assisted Process in the Batch Mode

Raw Material

The chokeberry (*Aronia melanocarpa*) residual pomace after pressing for juice production was provided by Elkøholm (Kolding, Denmark) and stored at −20° C. and thawed at 5° C. prior to the experiments. Moisture content was determined by weighing the difference in mass before and after a drying process (Memmert, Germany) at a temperature of 110° C. and found to be 62.4 grams per 100 grams of total material. All batches were homogenized using a laboratory grinder GM 300 (Retch, Haan, Germany). The dried pomace samples before and after enzymatic treatment presented a mean diameter ($d_m$) of about 970 and 140 μm, respectively.

Set-Up and Description of Enzyme-Assisted Extraction Process

Extraction experiments were carried out in a 1.0 L reactor equipped with a mechanical stirrer RZR 2050 (Heidolph, Schwabach, Germany, mixing velocity of 300 rpm) in an external water bath for temperature control. All experiments were carried out in dim light.

In the first-step experiments, the effect of enzymatic treatment on anthocyanin content was investigated. As shown in Table 1, the commercial juice-processing enzymes used in this study were provided by Erbslöh and AB Enzymes companies. Based on the suitable pH and temperature recommended for enzymes used in the present work as well as the results obtained from preliminary non-enzymatic experiments (data are not shown), the optimal operating conditions and extraction time were chosen.

For each experiment, 10 g of homogenized ground pomace was mixed with 500 g buffer solution (0.1 M Citric Acid-0.2 M $Na_2HPO_4$, pH=3) keeping the mixture at a ratio of 1:50 g pomace/g solvent. All the extraction experiments were carried out by adding the recommended enzyme dosage from the supplier and to be sure that the fully depectinization happened at temperature of 50° C. (except in the case of Fruktozym Flux where the effect of lower temperature was examined). During the extraction process, pigmented samples were collected each 10 min for 2 hours and then kept at −20° C. for further analysis.

In this step, beside the profile and concentration of anthocyanin in extracts, anthocyanin absorbance, total phenolic compounds (TPC) and sugar content as well as antioxidant activity (AA) was also measured. The mixture of pigmented extracts was centrifuged at 1000 rpm for 15 min in order to remove the particles while the supernatant was used for the purification step.

TABLE 1

Temperatures and pH recommended for the enzymes applied in the present experiment

| Enzyme name | Recommended Temperature (° C.)/ Reaction time (h) | Recommended pH | Production strain | Activity |
|---|---|---|---|---|
| Rohapect* | 50/1-3 | Recommended for low pH-juices | *Aspergillus niger* | Pectolytic |
| Fruktozym BE** | 45-55/1-2 | 3-5 | *Aspergillus niger* | Pectinase, 1,3(4)-β-glucanase |
| Fruktozym Flash-C** | 35-55/1-3 | 3-5 | *Aspergillus niger* | Pectinase, Arabino (2) galactanase, Rhamnogalcturonase |
| Fruktozyme Flux** | 45-55/1-2 | 3-5 | *Aspergillus niger* | pectolytic |

(*Supplied AB Enzymes GmbH, Darmstadt, Germany.
** Supplied by Erbslöh, Geisenheim, Germany)

Anthocyanin Identification and Quantification

Identification of anthocyanins in the samples was carried out by means of a UV-Visible spectrophotometer DR 3900 (Hatch, Düsseldorf, Germany) and high performance liquid chromatography (HPLC) (HP 1200 series, Agilent Technologies Aps, Nørum, Denmark). Separation was performed on a reverse phase C18 column (Gemini 5 µC18 110A, 250×4.6 mm i.d., Phenomenex Aps, Værløse, Denmark) equipped with a guard column (Security Guard System for C18, Phenomenex Aps, Vrløse, Denmark) at 25° C.

HPLC was equipped with a photodiode array detector. 0.05% v/v trifluoroacetic acid (TFA) in water (A) and 0.05% TFA in acetonitrile (B) was used as mobile phase at the flow rate of 1 ml/min. Gradient program was: 0-10% B (1 min), 10-20% B (19 min), 20-40% B (20 min), 40-80% B (10 min), 80-100% B (2 min), and 100%-0 B (1 min). Sample injection volume of 20 µl and a UV wavelength of 520 nm were used for detection. Peak assignment was performed by comparing the retention times and line spectral properties obtained from photodiode array detection with standards, Cy 3-galactoside, Cy 3-arabinoside, Cy 3-glucoside (Extrasynthese, France), and Cy 3-xyloside (Carbosynth, USA). All solvents were of HPLC grade (VWR Prolabo, Denmark). For absolute quantification, known concentration of each standard was used.

Total Phenolic Compounds

Total phenolic (TP) content of the samples was measured spectrophotometrically (DR 3900, Hatch, Düsseldorf, Germany) using gallic acid as standard, according to the method described by Sun, Powers, and Tang 2007. Briefly, Folin-Ciocalteau reagent was diluted 10 times using deionized water. The diluted reagent (0.75 mL) was mixed with 0.1 mL sample and held at room temperature for 5 min. 0.75 mL of 2% sodium carbonate solution was then added. The samples were kept for 15 min at room temperature, before the absorbance was measured at nm. The TP concentration in samples was derived from a standard curve of gallic acid and expressed as gallic acid equivalent (GAE) in g/100 g of material.

Antioxidant Activity Assay with DPPH

Antioxidant activity of samples and standard compounds (x as a major anthocyanin in the Aronia pomace) was determined by 2,2-diphenyl-1-picrylhydrazyl radical (DPPH) assay. The method used was according to the methods described by Devi et al. 2011 and Scherer and Godoy 2009. First, methanolic solution of DPPH was prepared by dissolving 24.5 g of the DPPH in 500 mL of methanol to reach to the molar concentration of 0.124 mM. DPPH methanolic solution (3.9 mL) was then added to 0.1 mL of the samples. Further, a blank sample prepared to be used as the reference: 0.1 mL of methanol was added to 3.9 mL of DPPH methanolic solution. The absorbance was measured using the spectrophotometer at 516 nm after 7 hours incubation at room temperature in the dim light. The radical scavenging activity (I %) was calculated as follows:

$$I\% = \left[\frac{Abs_0 - Abs_1}{Abs_0}\right] \times 100$$

where $Abs_0$ is the absorbance of the blank at time zero and $Abs_1$ was the absorbance of sample after 7 hours. Methanolic solutions of the sample was made at ratio of 1:2 (sample: methanol).

Example 2

Profile of anthocyanins in Aronia pomace

HPLC analysis identified four different anthocyanins in all the Aronia pomace extracts: Cyanidin 3-galactoside, Cyanidin 3-glucoside, Cyanidin 3-arabinoside, and Cyanidin 3-xyloside, with Cyanidin 3-galactoside being the predominant compounds followed by Cyanidin 3-arabinoside (Table 2). As also seen in Table 2, it is worth mentioning that regardless of the total anthocyanin concentration the proportion of anthocyanins exist in the pomace extract was not significantly affected by the enzymes used in the present work where the galactocides and arabinosides of cyanidin contain respectively about 60% and 30% of the total anthocyanins in non-enzyme or enzyme-assisted extraction process. Further, the profile of anthocyanins in the Aronia pomace used in the present study is similar to that reported in previous studies.

Example 3

Enzyme-Assisted Extraction Process in the Batch Mode (Choosing the Appropriate Enzyme)

The effect of different enzymes on absorbance, anthocyanins concentration, total phenolic compounds, and antioxidant activity was shown in Table 1 and Table 2 (below).

TABLE 2

Effect of different enzymes on extraction of anthocyanins from Aronia pomace (TAC: total anthocyanin concentration; AC: anthocyanin)

| Arranged No. | Enzyme name | Temperature (° C.) | Tested Enzyme concentration (mL/ton) | Absorbance (510 nm) | AC conc. (mg/L) Cy 3- galactoside | AC conc. (mg/L) Cy 3- glucoside | AC conc. (mg/L) Cy 3- arabinoside | AC conc. (mg/L) Cy 3- xyloside | TAC (mg/L) |
|---|---|---|---|---|---|---|---|---|---|
| 1 | — | 50 | — | 2.1 ± 0.09 | 136.3 | 7.5 | 65.4 | 10.1 | 219.3 ± 3.04 |
| 2 | Rohapect | 50 | 400 | 2.2 ± 0.02 | 150.7 | 9.6 | 73.7 | 12.1 | 246.1 ± 8.18 |
| 3 | Fruktozym BE | 50 | 400 | 2.3 ± 0.11 | 166.6 | 10.7 | 81.3 | 13.2 | 271.7 ± 0.12 |
| 4 | Fruktozym Flash C | 50 | 400 | 2.3 ± 0.08 | 209.2 | 13.4 | 103.0 | 13.2 | 343.1 ± 45.91 |
| 5 | Fruktozym Flux | 50 | 400 | 2.3 ± 0.08 | 222.7 | 14.3 | 110.9 | 18.9 | 366.8 ± 15.89 |
| 6 | Fruktozym Flux | 30 | 400 | 1.5 ± 0.04 | 154.8 | 9.3 | 72.8 | 11.5 | 248.4 ± 15.75 |

The total anthocyanin concentration in Aronia pomace was increased in all the enzyme-assisted extraction experiments. The most efficient enzyme regarding the total extracted anthocyanins was Fruktozym Flux, increasing the anthocyanin extraction yield nearly 68% while for the other enzymes the increase was between 12 and 36%. On the other hand, as shown in Table 2, the enzyme addition did not have significant effect on the absorbance of the pigmented samples while decreasing the temperature from 50 to 30° C. resulted in decrease of anthocyanins concentration and extract absorbance from 367 to 248 mg/L and 2.3 to 1.5, respectively.

These surprising observations are in contrast to observations from the prior art suggesting lower optimum temperature, such as 30-35° C., for extraction of anthocyanins from whole black currant berries. However, increasing the temperature resulted in lower buffer solution viscosity which enhances the diffusivity coefficient. Consequently, the rate of the mass transfer of anthocyanins from Aronia pomace to the buffer solution and its corresponding absorbance and concentration in the pigmented extract will increase (Table 2). Therefore, it can be concluded that in these observations of the present experiments for enzymatic extraction of anthocyanins from Aronia, the thermal degradation of anthocyanins did not increase with temperature as fast as the extraction efficiency increased.

Moreover, the enzymatic improvement of phenolic compounds concentration was evident in experiments at 50° C. with Rohapect as the most effective enzyme (Table 3). In addition, decreasing the temperature from 50 to 30° C. causes the total phenol content reduction by half; i.e. from 469 to 228 ppm. The ratio of total extracted anthocyanin to total phenolic compounds was also shown in Table 3. The results suggest selective release of compounds from Aronia pomace to the buffer solution which can be related to the difference in the activity of the enzymes used in this study. Among the four different enzymes, the purity of the anthocyanins is the most (0.8 and 1 at 50 and 30° C., respectively) using Fruktozym Flux, while considering the high content of phenolic compound in the experiment no. 2, applying Rohapect resulted in the lowest ratio. Further, the addition of enzyme did not have a significant effect on the antioxidant activity of the extracts. In the prior art the effect of phenolic compounds and anthocyanins extracted from chokeberry on the extract's DPPH scavenging activity has been investigated and it has been found out that there is a stronger correlation between the DPPH scavenging activity and phenolic compounds than anthocyanins. Hence, the slight decline of the $\Delta\lambda$ index in the experiments no. 4 and 5 can be explained by dependency of the antioxidant activity more on the phenolic compounds content in the pigmented samples than the anthocyanins.

Therefore, the pigmented sample after enzyme-assisted extraction process using Fructozym Flux was centrifuged and purified to be used for evaluation of the effect of co-pigmentation on the stability of the colorant.

TABLE 3

Effect of different enzymes on extraction of total phenolic compounds and antioxidant activity

| Arranged No. | TPC (ppm) | TAC/TPC | AAI (%) |
|---|---|---|---|
| 1 | 420.8 ± 13.00 | 0.52 | 48.0 ± 0.96 |
| 2 | 573.3 ± 15.98 | 0.43 | 47.5 ± 1.58 |
| 3 | 505.6 ± 11.34 | 0.54 | 49.9 ± 4.44 |
| 4 | 492.6 ± 12.33 | 0.70 | 43.6 ± 1.47 |
| 5 | 469.1 ± 5.65 | 0.78 | 24.0 ± 0.39 ± 2.69 |
| 6 | 227.9 ± 91.55 | 1.09 | 24.0 ± 0.39 |

(TPC: Total phenolic compounds (results are expressed as mg gallic acid equivalents per 100 g of material), TAC: total anthocyanins compounds AAI %: Antioxidant activity index)

Effect of Adding Co-Pigment on Enzymatic Extraction Process in the Batch Mode

In order to analyze the effect of co-pigment addition on enzymatic extraction of total anthocyanin (TAC) and phenolic compounds (TPC), ferulic acid at three different ferulic acid: anthocyanin molar ratios of 66, 100, and 175 was added to the mixture of Aronia pomace: buffer solution (1:50 w/w). As seen in Table 4, the experiments were carried out at the optimal conditions found in the previous enzymatic extraction experiments: 400 ppm Fruktozym Flux and temperature of 50° C. for about 45 min. Rohapect was also tested to check the effect of co-pigmentation. As shown in the Table 4 (below), the anthocyanin concentration in the extract increased significantly in the both cases of enzymes. Using Rohapect as an enzyme and addition of ferulic acid: anthocyanin molar ratio of 100 resulted to increase the TAC yield from about 246 to 352 mg/L. In the case of Fruktozyme the molar ratio of 66 showed the highest effect on the TAC yield i.e. from 367 to 398 mg/L. Therefore, the results prove the concept that adding co-pigment can improve the stabilization of anthocyanin during the extraction along with reduction of the inhibitory effect (see FIG. 4) and hence it can be concluded that co-pigmentation can increase the TAC extraction yield. The less increase of the TAC in the case of using Fruktozym Flux can be explained by saturation of the solvent to the limit that no more anthocyanin can be extracted from the pomace to the solvent and so reducing the rate of extraction. Hence, more experiments are required to optimize the experiments condition, in particular, the pomace: buffer ratio and co-pigment factor and its concentration.

TABLE 4

Effect of different ferulic acid: anthocyanin molar ratio on enzymatic extraction of anthocyanins from Aronia pomace

| Enzyme name | Temperature (° C.) | Enzyme concentration (mL/ton) | Ferulic acid: anthocyanin molar ratio | Absorbance (510 nm) | AC conc. (mg/L) Cy 3-galactoside | AC conc. (mg/L) Cy 3-glucoside | AC conc. (mg/L) Cy 3-arabinoside | AC conc. (mg/L) Cy 3-xyloside | TAC (mg/L) |
|---|---|---|---|---|---|---|---|---|---|
| Rohapect | 50 | 400 | 100 | 2.7 ± 0.01 | 214.1 | 13.0 | 108.4 | 17.0 | 352.5 ± 3.27 |
| Fruktozym Flux | 50 | 400 | 175 | 2.6 ± 0.00 | 213.0 | 13.4 | 106.5 | 17.6 | 350.4 ± 16.1 |
| Fruktozyme Flux | 50 | 400 | 100 | 2.7 ± 0.10 | 214.8 | 13.5 | 111.1 | 17.0 | 356.3 ± 2.69 |
| Fruktozyme Flux | 50 | 400 | 66 | 2.8 ± 0.07 | 240.8 | 15.3 | 121.7 | 20.1 | 397.8 ± 7.93 |

Example 4

Co-Pigment and Enzymatic Assisted Extraction Process Using Membrane Bioreactor in Semi-Continuous Mode Set-Up Information and Description of the Process The hydrolysis of aronia pomace was carried out in a MBR (BIOSTATR B sartorius) which consisted of a 5-L glass vessel as the main reactor connected to an ultrafiltration system equipped with ceramic membrane (Inopore) of 20 KDa MWCO and surface area of 0.011 m². The reaction mixture was continuously recycled from the reactor to the membrane module by using a pump and the reactor volume was kept steady by means of an automatic level control. As mentioned before, considering the molecular weight of sugars (Sorbitol, Fructose, and Glucose; approx. 180 g/mol), anthocyanins (Cy 3-galactoside, Cy 3-glucoside, Cy 3-arabinoside, Cy 3-xyloside; approx. 450 g/mol), and galacturonic acid (194 g/mol), these compounds will pass through the 20 KDa membrane while enzymes and pomace with higher particle size than 20 KDa will be rejected and recycled to the reactor.

In addition, the temperature (50° C.) and agitation of reactor (300 ppm) was automatically controlled. Hydrolysis experiments were conducted by first adjusting the temperature of the 5 L buffer solution, and then loading the reactor tank with the ground pomace at required concentration (Pomace: buffer solution ratio of 1:50). Afterwards, the enzyme solution was added at different concentration, starting with 400 ppm (based on the data in the batch mode) and increasing to 2000 ppm. The operating conditions of runs were as follows: ubstrate-to-enzyme ratio, pH 3 (0.1 M Citric Acid-0.2 M $Na_2HPO_4$), 50° C., 300 rpm, recycling flow rate of approx. 25 L/min, and a transmembrane pressure of about 1 bar.

More detailed information regarding the membrane bioreactor, enzyme and membrane used in this work can be seen in Table 5.

TABLE 5

Experimental set-up information regarding the membrane bioreactor, enzyme and membrane used in the experiments

| Fermentor | |
|---|---|
| Volume capacity (L) | 5 |
| Buffer solution | Citric Acid - $Na_2HPO_4$ |
| Temperature (° C.) | 50 |
| Pomace to Buffer ratio | 1:50 |
| pH | 3 |
| Company (model) | BioStat B |

TABLE 5-continued

Experimental set-up information regarding the membrane bioreactor, enzyme and membrane used in the experiments

| Enzyme | |
|---|---|
| Name | Fruktozym Flux |
| Concentration (ppm) | 400, 1200, 2000 |
| Company | Erbslöh |
| Membrane | |
| Molecular cut-off (KDa) | 20 |
| Material | Ceramic - $Al_2O_3$ |
| Membrane area (m²) | 0.011 |
| Company | Inopor |

Effect of Adding Enzyme and Cofactor at Different Concentration on Anthocyanin Extraction Yield in the First One Hour of the Reaction in the MBR Three different enzyme concentrations have been studied in the first hour of the reaction occurred in the bigger scale reactor (5 L). It is worth reminding the point that the 1 hour reaction is before connection of the reactor to the membrane. As can be seen in Table 6, in general, the addition of enzyme concentration from 400 to 2000 ppm increased the AC yield in the reactor.

In the batch experiments the effect of cofactor in increasing the AC extraction yield was observed at the molar ratio of 66 (Table 4). However, while performing the scale-up experiments the cofactore dosage had to be adjusted differently. Therefore, to check the effect of copigment, ferulic acid was added at the molar ratio of 1:10 to TAC content. Hence, 6.4 g of ferulic acid was added to the reactor meanwhile adding 2000 ppm enzyme and as can be seen it could improve the extraction yield from about 305 to 360 ppm.

TABLE 6

Effect of addition of three different Fruktozym Flux concentration and copigment on the total anthocyanin concentration (mg/L) in the reactor (before starting the MBR)

| | Concentration of enzyme (ppm) | | | | |
| --- | --- | --- | --- | --- | --- |
| Time (min) | No-enzyme | 400 | 1200 | 2000 | 2000 + copigment |
| 0 | 140.7 ± 9.16 | 235.6 ± 30.55 | 263.8 ± 7.8 | 173.5 ± 12.55 | 218.8 ± 21.78 |
| 20 | 242.5 ± 40.24 | 222.6 ± 3.73 | 281.0 ± 0.78 | 285.9 ± 22.00 | 321.8 ± 16.61 |
| 40 | 254.8 ± 54.04 | 224.8 ± 2.17 | 285.6 ± 21.25 | 305.0 ± 19.19 | 342.1 ± 15.02 |
| 60 | 246.9 ± 41.23 | 203.1 | 261.1 ± 20.51 | 305.0 ± 12.46 | 360.1 ± 35.5 |

Effect of Addition of Enzyme on the Juice Flux During the MBR Process

Figure 3:
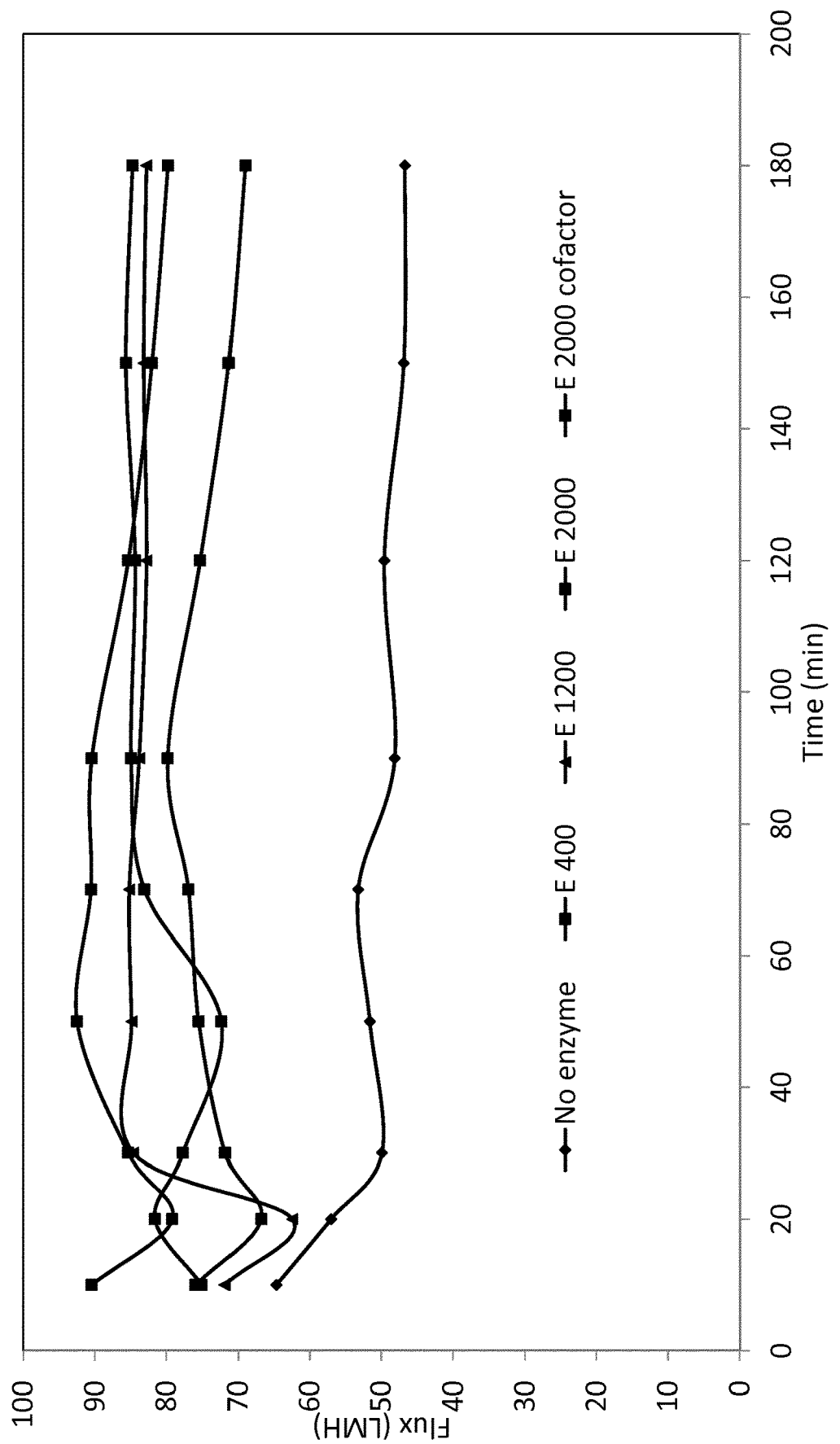
FIG. 3 shows the effect of adding co-factor and enzyme on the Juice flux in the e-MBR.

As shown in FIG. 3, the juice flux has been recorded during the three hours MBR reaction. It is obvious that the addition of enzyme resulted in decrease of the particle size distribution of pomace. The laser measurements showed that the dried pomace samples before and after enzymatic treatment presented mean diameter ($d_m$) of about 970 and 240 µm, respectively. Therefore, less fouling has been occurred during the filtration process and the flux has been increased significantly compared to the flux without enzyme. Moreover, addition of copigment resulted in marginal decrease of the flux that can be related to the more suspended solid in the solution and/or formation of the slightly bigger molecules that cause the pore blocking. However, the juice flux is still higher compared to the flux while no addition of enzyme.

The membrane recovery was almost 100% after addition of enzyme.

Figure 4:
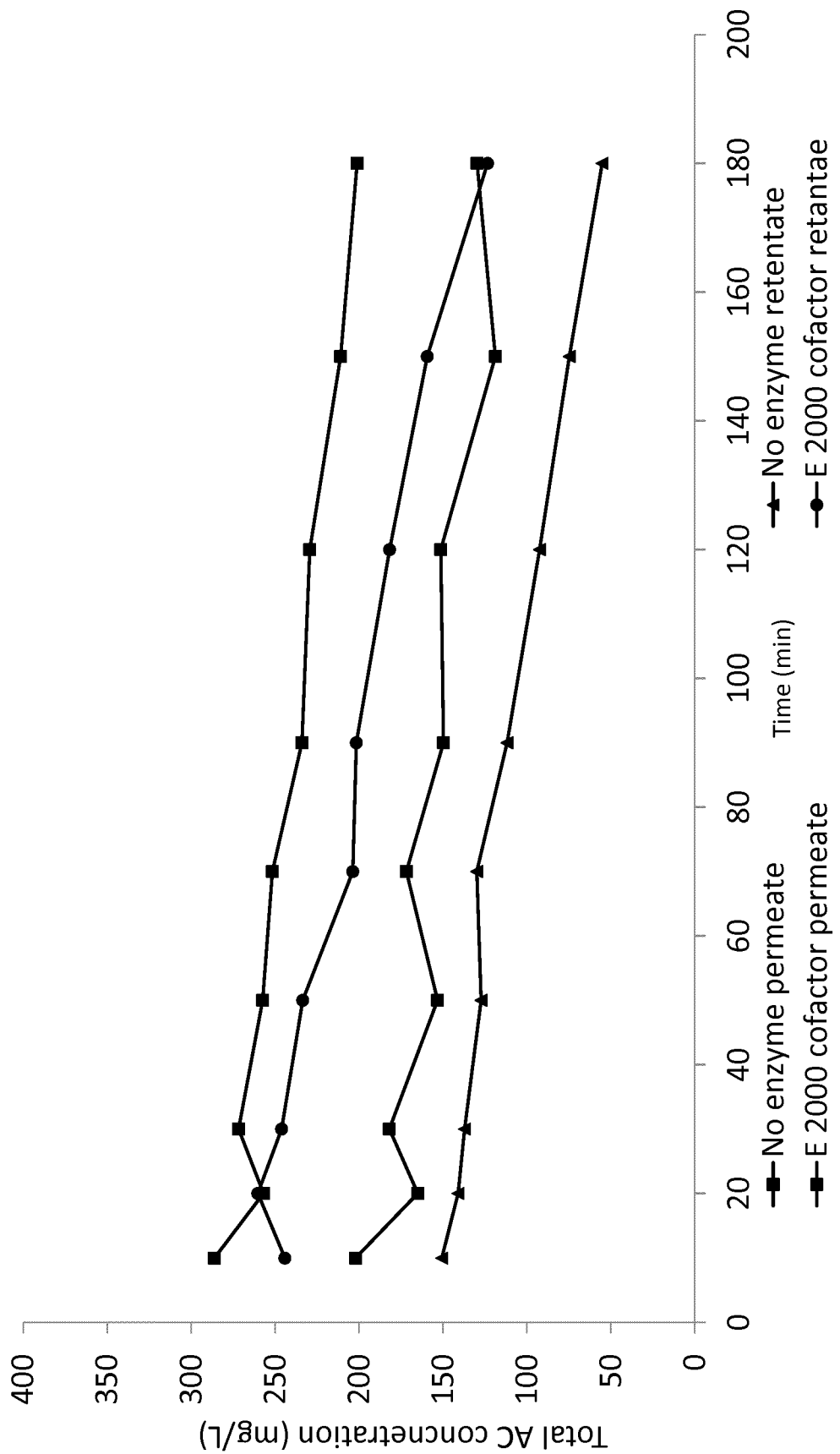
FIG. 4 shows total anthocyanin concentration (TAC; mg/L) of permeate and retentate during the e-MBR in one cycle, showing that addition of copigment and enzyme resulted in higher extraction yield.
Figure 5:
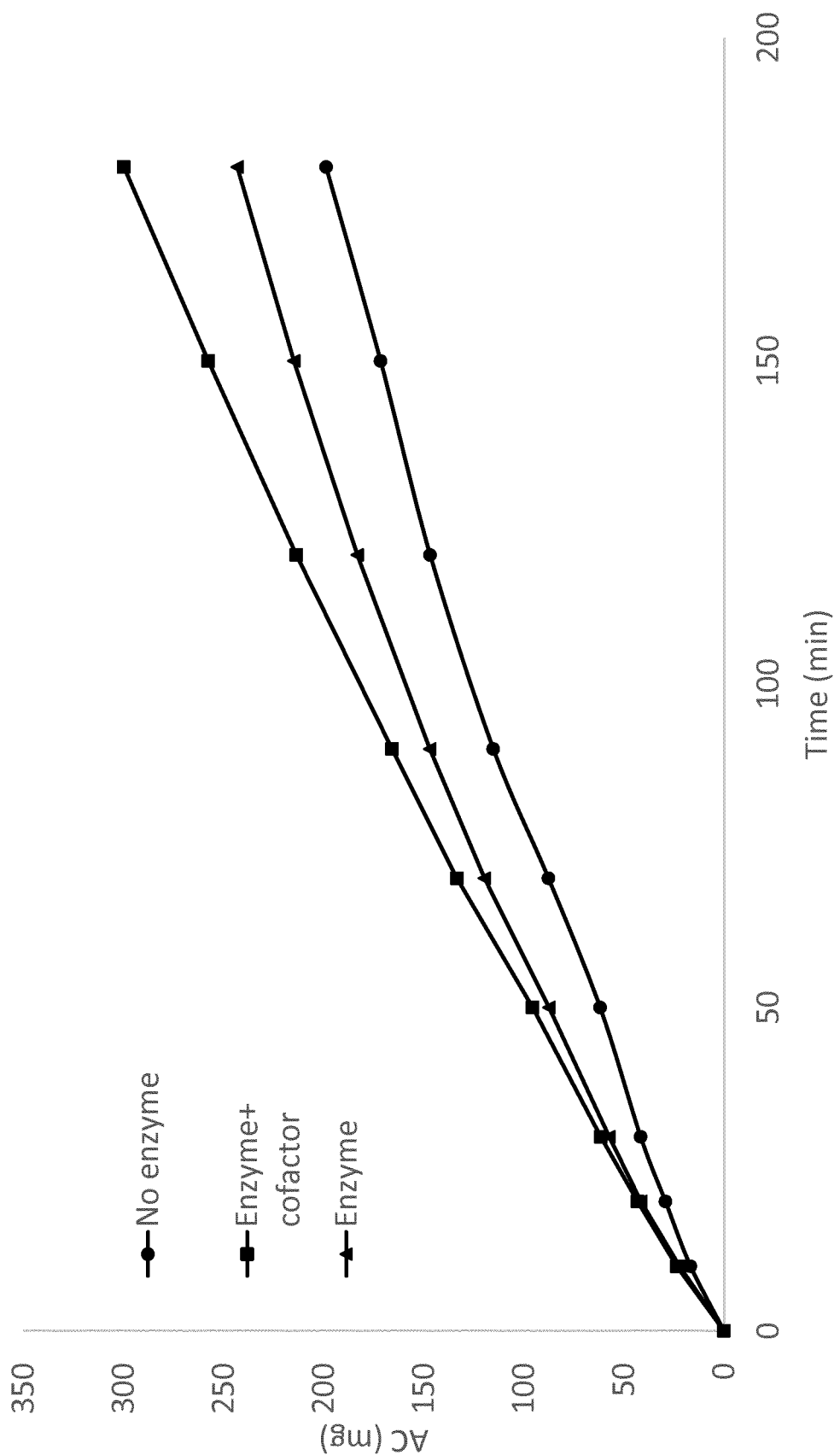
FIG. 5 shows the effect of the enzyme, and enzyme+ copigment on anthocyanin content (mg) of permeate during the e-MBR. It shows that combination of enzyme and copigment can improve the degradation of anthocyanin during the extraction along with reduction of the inhibitory effect and hence it can be concluded that co-pigmentation can increase the TAC extraction yield.

Total Anthocyanin Concentration (Mg/L) During the MBR Process Before and after Addition of Enzyme and Co-Factor-One Cycle As shown in Table 2 and 4, the experiments carried out in small scale (500 mL) reactor proved that addition of enzyme and co-factor resulted in increase of AC yield. In this part of the experiments, the effect of enzyme (2000 ppm was chosen based on the results from Table 6) and co factor (Ferulic acid: TAC content molar ratio of 1:10) on the AC concentration in the permeate and retentate during the MBR was studied. As shown in FIG. 4, during the three hour MBR process, the AC concentration in permeate of the process with enzyme was higher than the one without enzyme addition. Moreover, FIG. 5 shows the effect of addition of enzyme and enzyme plus cofactor in increasing the AC content compared to non-enzymatic reaction. As can be seen, the AC content changed from 200 mg for non-enzymatic process to and 300 mg in the permeate by adding the enzyme and enzyme plus cofactor, respectively.

That can prove the fact that cofactor has the preservation effect during the reaction and retard the AC degradiation during the process. On the other hand, based on the molecular weight of the galacturonic acid, using MBR, it is expected that they also pass through the membrane and hence their inhibitory effect on the hydrolysis reaction will be reduced.

Figure 6:
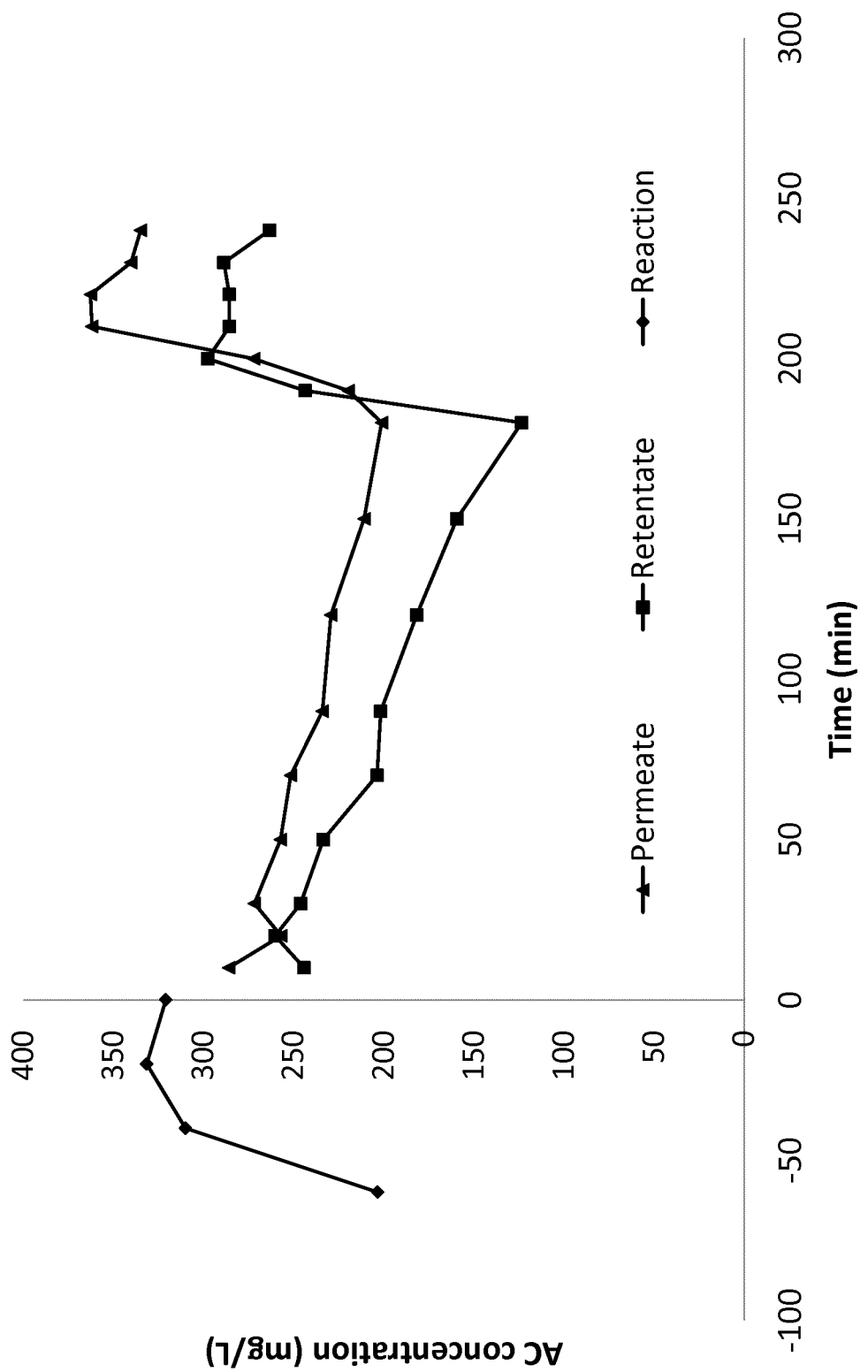
FIG. 6 shows the total anthocyanin concentration (TAC; mg/L) in the permeate and retentate in the first and second cycle showing the possibility of continuously adding fresh pomace during e-MBR while no need for addition of enzyme.

Addition of New Batch pomace to the Reactor after Three Hours MBR Process-Second Cycle To be able to check the activity of enzyme and possibility of running the MBR in a longer period, after three hours MBR process, extra 100 g fresh pomace was added to the reactor. As shown in FIG. 6, the AC concentration (mg/L) increase in both permeate and retentate after pomace addition whereas stated to decline similar to the first cycle after sometimes. Hence, applied enzyme is still active and there is no need to add extra enzyme as in the batch mode reaction. Also it can prove the fact that enzymes were rejected by membrane and recycled to the reactor vessel during the process. Moreover, it shows that it can be possible to decrease the pomace:buffer solution ratio lower than 1:50 to achieve even more optimum operating condition.

Example 5

Purification Process
Nanofiltration for Partial Sugar/Anthocyanin Separation

Figure 7:
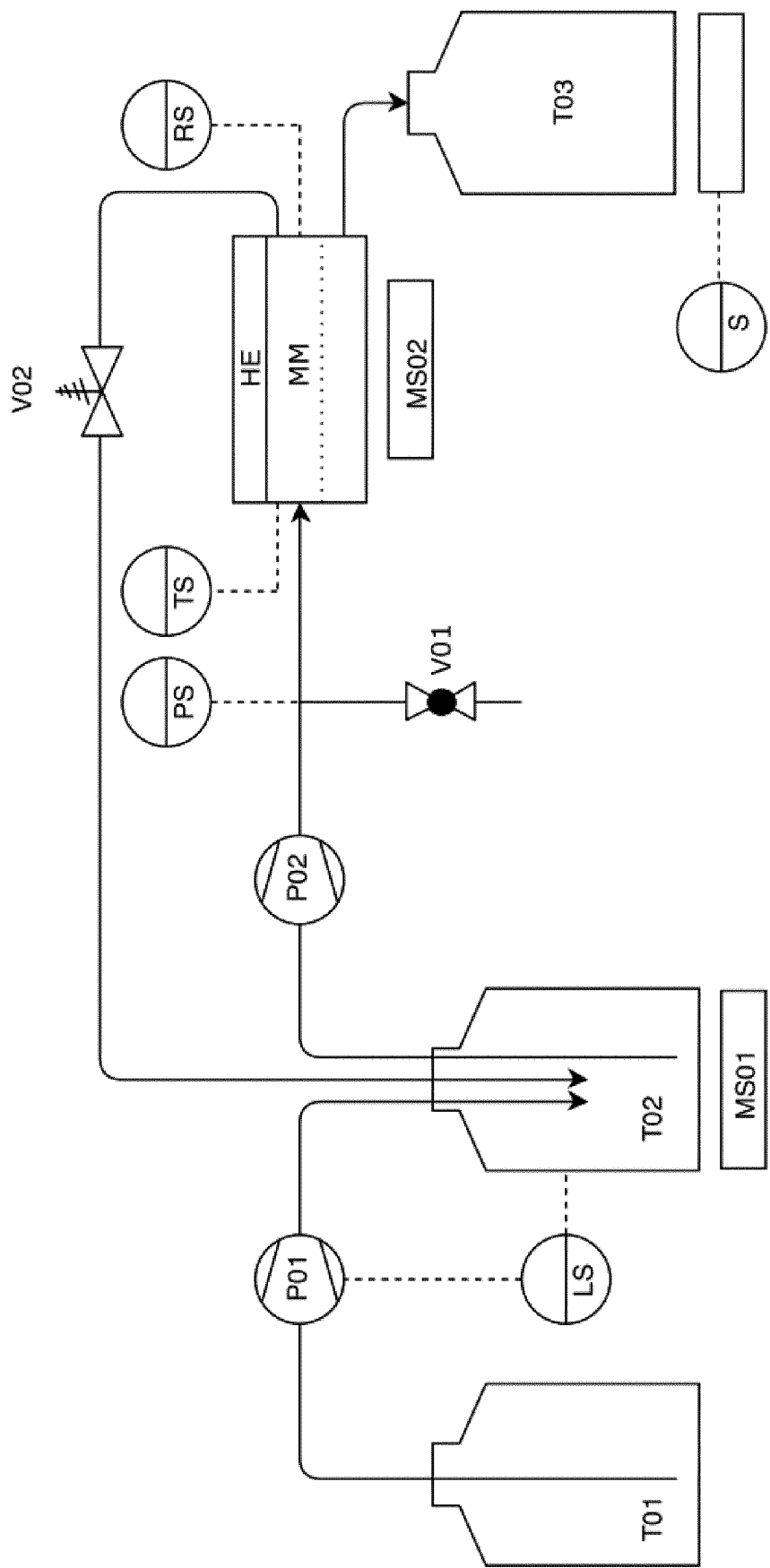
FIG. 7 shows the set-up used for dia-nanofiltration (dia-NF) of the anthocyanin extract for partial purification of anthocyanins.

In order to check the possibility of purification/concentration of anthocyanins in extracts, three different membranes have been tried. The purpose of the trials was to reach the highest rejection of anthocyanins in the retentate while separating sugar, salt, and galacturonic acid in the permeate. The membranes have been selected considering the average molecular weight of anthocyanidin (approx. 450 g/mol) and sugars (180 g/mol), and galacturonic acid (194 g/mol). For this purpose, three different membranes chosen for NF process are presented Table 7. The flow diagram of the process using MiniMem small scale set-up also can be seen in FIG. 7. All the experiments have been carried out while the feed flow rate was kept at 10 mL/min, temperature at 25° C. and a membrane area of 28 cm$^2$.

TABLE 7

General information of the membranes used for separation of sugar from anthocyanin

| Membrane type | Etna 01PP | GR 95 | RO 90 |
| --- | --- | --- | --- |
| Manufacturer | Alfa Laval | Alfa Laval | Alfa Laval |
| Membrane material | Composite Fluoro polymer | Polyethersulphone | Thinfilm composite |
| Molecular weight cut-off (Da) | 1000 | 2000 | >90% NaCl rejection |
| Max. Operating pressure (bar) | 10 | 10 | 42 |
| Max. Operating temperature (° C.) | 60 | 75 | 55 |
| Range of pH | 1-11 | 1-13 | 3-10 |

Figure 8:
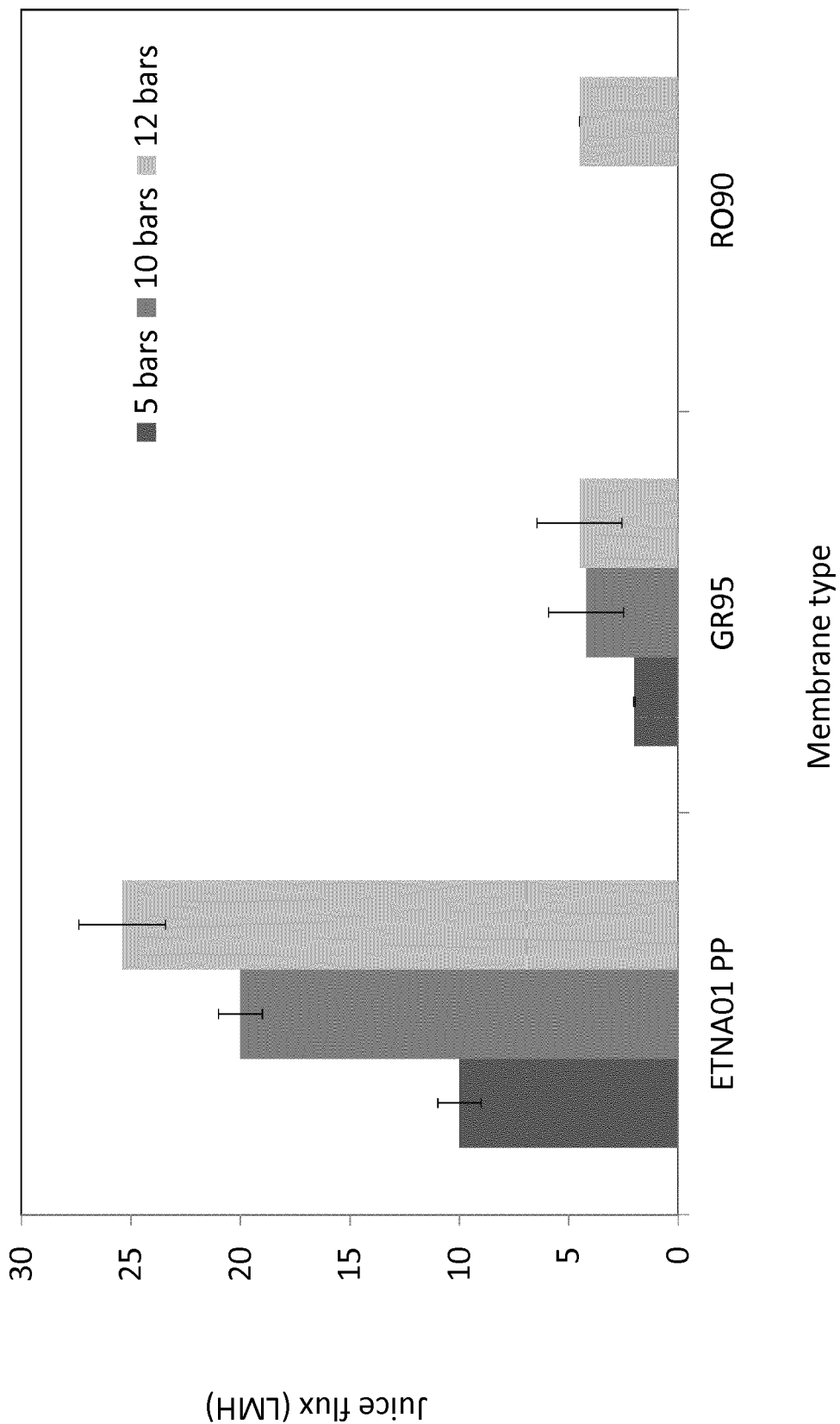
FIG. 8 shows the juice flux using three different NF membranes, ETNA01 PP, GR95, R090, at three different pressure of 5, 10 and 12 bars.

In FIG. 8 juice flux at three different pressure of 5, 10, and 12 bars using the three mentioned membranes were shown.

In general, the juice flux of the Etna 01PP was the highest compared to two other selected membranes. The low flux from RO 90 was expected because of the dense structure of the membrane and therefore smaller pore size. Whereas, the MWCO of the GR 95 is higher than Etna 01pp, the flux is as low as about RO90. This different can be explained by the difference in the two membrane hydrophilicties. Moreover, it can be seen that increasing the pressure from 5 to 10 bars increased the flux while this increase was not significant by increasing the pressure from 10 to 12 bars (FIG. 8). In addition, the effect of pressure in the GR 95 was not also significant. Using Ro, the pressure has to increase above 12 bars to be able to see the permeate flux.

After each experiments, the AC and sugar rejection was calculated using the equation of $Rj_i(\%)=1-Cp_i/Cf_i \times 100$; Where $Rj_i$ is the rejection percent of i, $Cp_i$ is the concentration of i in the permeate at the end of the filtration and $Cf_i$ is the concentration of i in the feed before starting the filtration. The most suitable membrane in this part of the experiments is the membrane that has the highest rejection for TAC but the lowest for sugar.

Figure 9A:
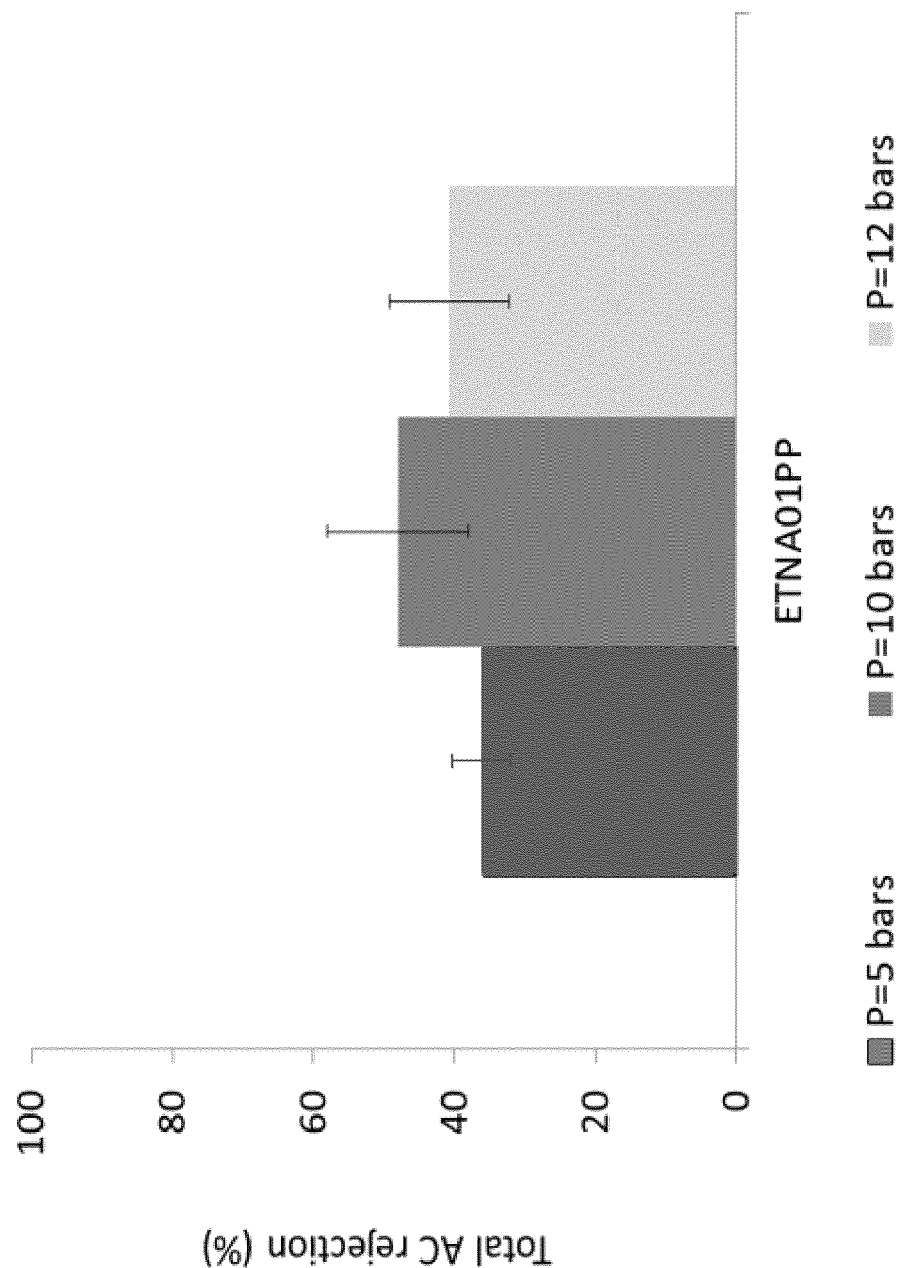
FIG. 9 shows the total anthocyanin (AC) rejection (%) using Etna01pp (FIG. 9a) and GR 95 (FIG. 9b) at three different pressure (5, 10, and 12 bars).

The total AC (TAC) and total sugar rejection using Etna 01pp and GR 95 at different pressure was shown in FIGS. 9a,b and 10a,b. The optimum pressure was chosen to be 10 bars as more increasing the pressure also resulted in more forcing the AC to pass through the membranes and hence lower rejection. Besides, higher pressure means more energy and so to avoid the higher energy consumption in the process but still having a better separation, pressure of 10 was chosen as the best operating condition.

Figure 9B:
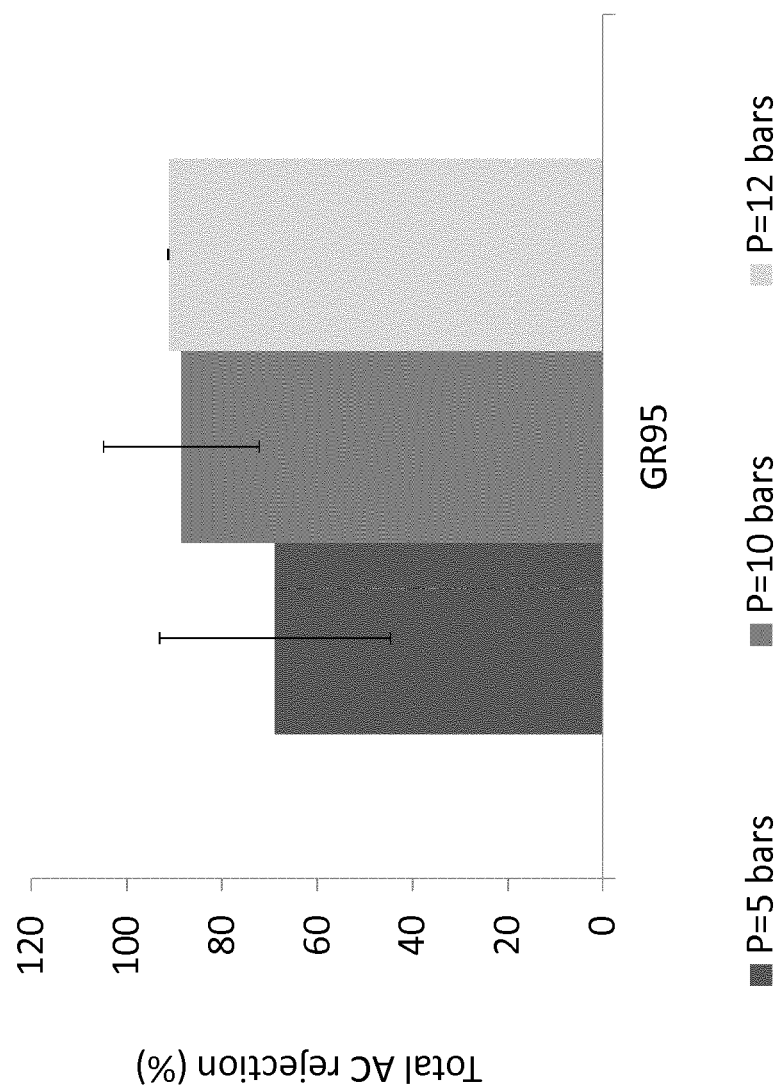
Figure 10A:
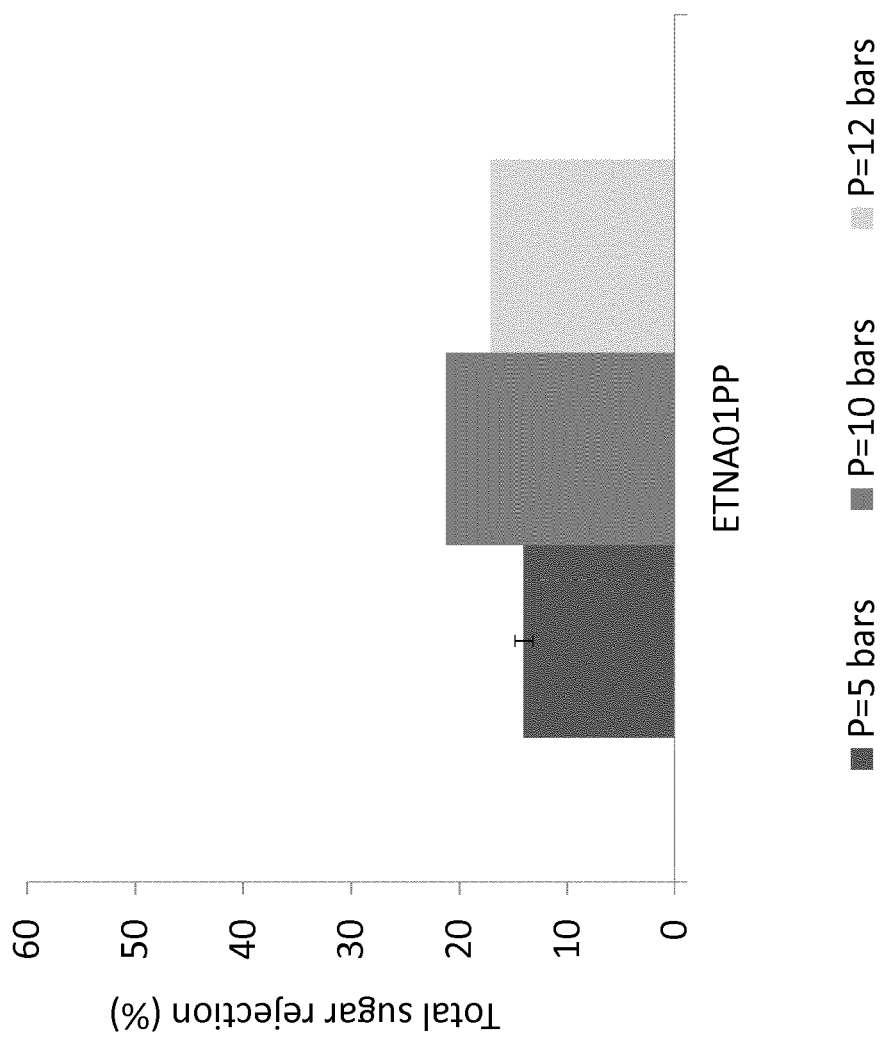
FIG. 10 shows the the total sugar rejection (%) using Etna01pp (FIG. 10a) and GR 95 (FIG. 10b) at three different pressure (5, 10, and 12 bars).
Figure 10B:
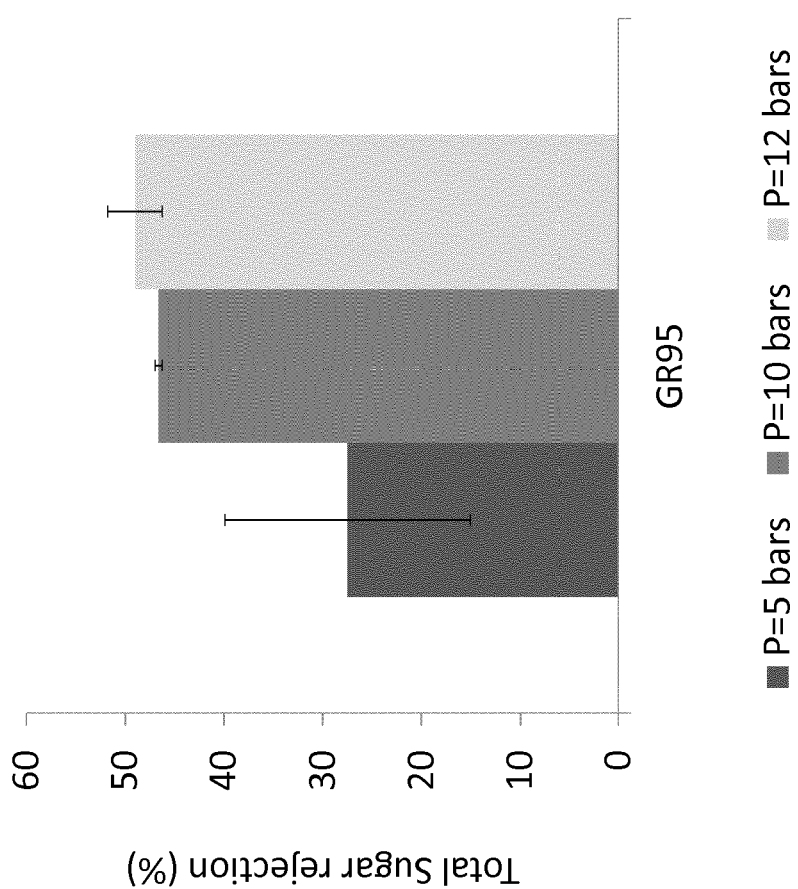

Regarding the TAC, although the TAC rejection was higher (approx. 88%) in GR 95 (FIG. 9b), the sugar rejection is also very high (approx. 50%) (FIG. 10b). In this regard, Etna 01pp showed more interesting results where the TAC rejection is about 50% and the sugar rejection can be achieved to be about 20%. Therefore, bearing in mind that the juice flux of the Etna 01pp was significantly higher than GR 95, Etna 01pp was chosen to check the effect of pH on the separation process (at pressure of 10 bar). At this condition the rejection of the total phenolic compound (equivalent to galic acid), total acidity (equivalent to citric acid), total soluble solid also measured to be about 20%; 25%, and 17%, respectively.

In addition, results regarding the RO 90 shows the 100% rejection of both TAC and sugar. Hence, the applicability of RO 90 can be limited to only concentration applications and not purification.

Figure 11:
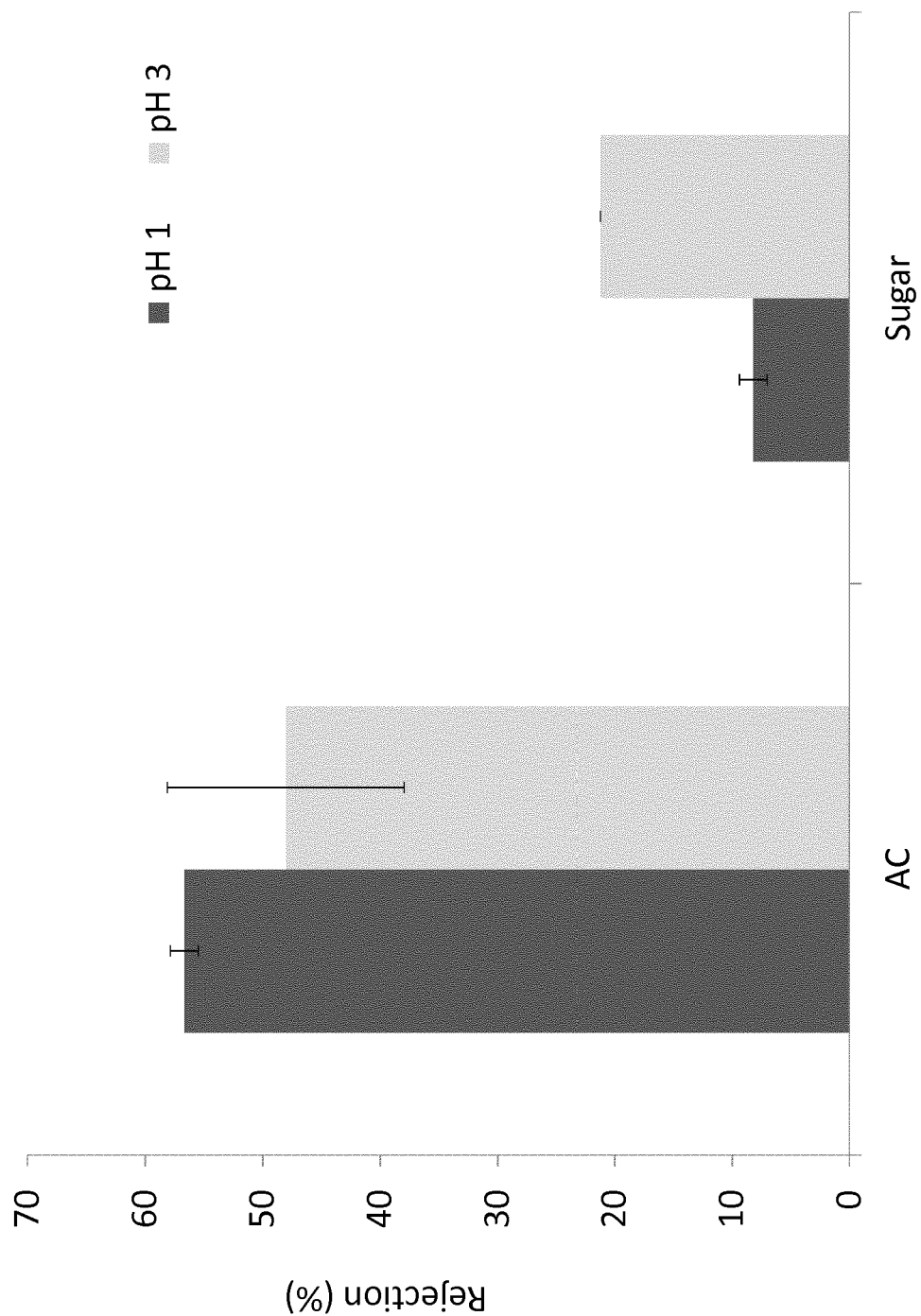
FIG. 11 shows the effect of pH (1 and 3) on AC and sugar rejection (%) using Etna01pp at a pressure of 10 bar.

As shown in FIG. 11, addition of citric acid and reducing the pH from 3 to 1 did not have a significant effect on the TAC rejection while decreasing the total sugar rejection (from 20% to 8%). This observation can be related to the fact that the anthocyanin's chemical structure is changing at different pH and has a positive charge at the pH of around 1. Therefore, the moiety of the anthocyanins also changed by pH reduction which cause the pass of sugar from the membranes easier.

Therefore, for a partial separation of the AC from sugar, using Etna 01pp at pressure of 10 bars and pH of 1 can be beneficial. In these conditions, it is feasible to separate 92% of the sugar from the anthocyanin extract solution and have a concentrate and more purified anthocyanin. In the process, depending on the purification demand, it is possible to use the diafiltration method, where by using the buffer solution we will be able to wash a higher amount of sugar/acid/and salts out of the mixture and hence obtain more purified anthocyanins.

Possibility of Affinity Chromatography to Remove Total Sugar

In the purification step, affinity chromatography was carried out to separate sugar from the anthocyanins. A non-ionic acrylic ester resin of moderate polarity (XAD7HP®, Sigma Aldrich, Denmark) was chosen. 5 g of the XAD7HP® resin was soaked in water, loaded to a 10 mL crystal column, and rinsed with water to remove small particles. To investigate the maximum adsorption capacity of the resin, different volumes of extract were loaded into the column until saturation was observed. After optimization, water-soluble impurities were washed out by rinsing the column with distilled water until no sugars were detected in the eluent with a glucose kit (Glucotest®). Afterwards, the adsorbed anthocyanins were eluted by several fractions of ethanol 96% (v/v) acidified with 1% (w/w) of citric acid monohydrate. Samples were collected and evaporated under vacuum at 35° C. using a rotary evaporator R-210 (Buchi, Flawil, Switzerland).

Figure 12:
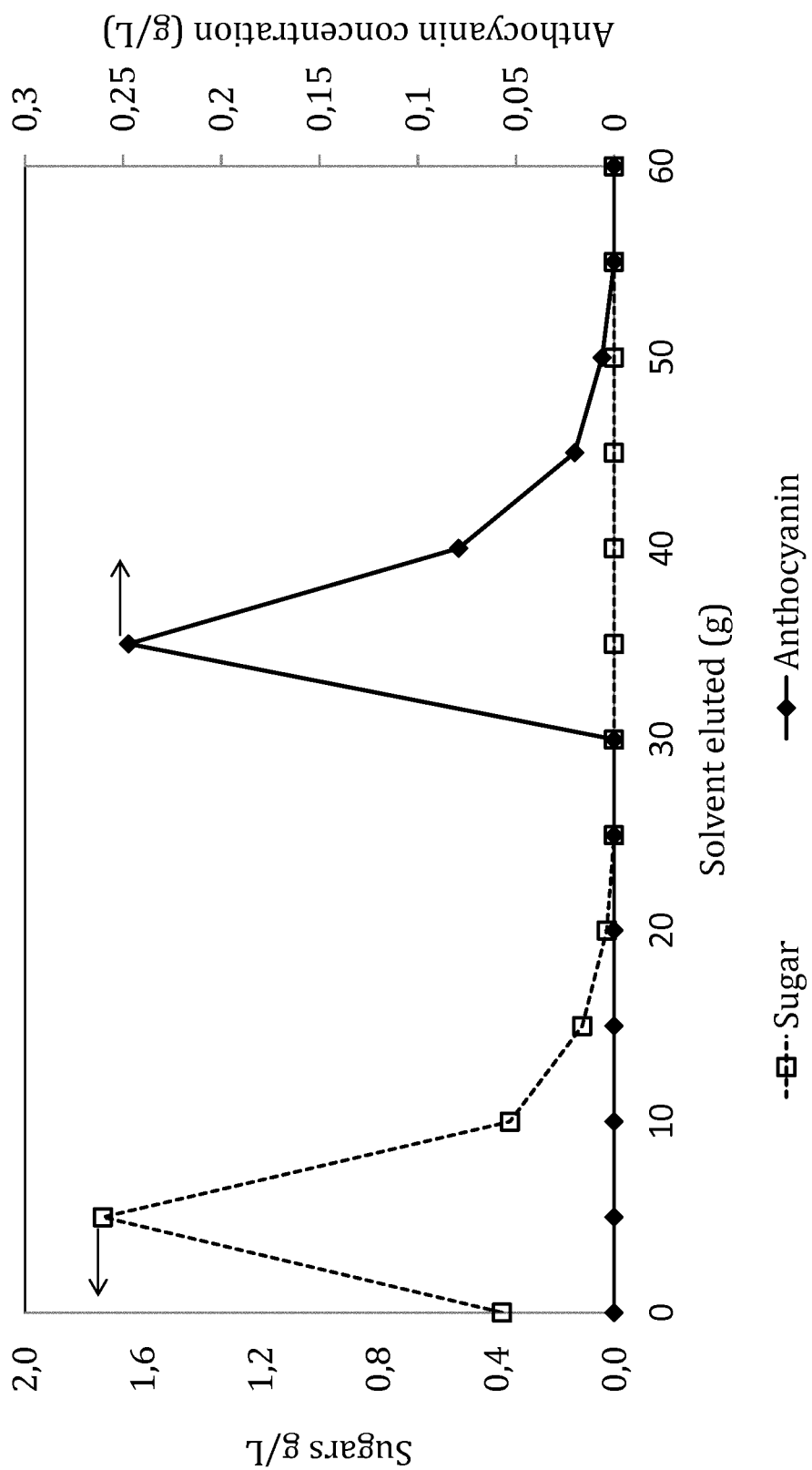
FIG. 12 shows elution profiles of sugars and anthocyanins after water (30 g) and acidified ethanol (30 g) elution of Aronia extract adsorbed over XAD7HP® resin; resulted in sugar separation of 96% and hence anthocyanin purification.

Adsorption and desorption capacities of anthocyanins on the resin was calculated at equilibrium to be approximately 0.4 and 0.98 mg of/g of resin, respectively (resin: extract ratio of 1). Concentration profiles obtained with both eluents used in this work are shown in FIG. 12. As shown in FIG. 12, the resin XAD7HP® showed the sufficient adsorption and desorption performances for anthocyanins which can be attributed to their similar polarity and its high solid phase surface area. Total sugars in the extract were washed out in the aqueous eluent (deionized water) after 30 mL was added while no anthocyanins were detected showing the strong bonds between the anthocyanins and the resin to withstand the water elution. Ethanolic elution provided efficient anthocyanins recovery of nearly 96%.

Example 6

Co-Pigmentation Process in the Batch Mode

One of the major challenges in storing the extracted aglycone AC for further applications is their low stability. Many factors affect the stability of anthocyanins such as temperature, pH, sugars and their degradation products. Higher stability is achieved by storing extracts at low pH (<3) and low temperature.

Ferulic acid (Sigma Aldrich, Denmark) was chosen as a co-pigment factor based on the results of our preliminary screening experiments (as an example, comparison of ferulic acid and sinapic acid shown in Table 8) as well as previous studies on co-pigmentation of cyanidins.

TABLE 8 comparison of ferulic acid and sinapic acid during one month as two potential aglycone anthocyanins' copigments

|  |  | Concentration ferulic (mM) | | | Concentration sinapic (mM) | | |
| --- | --- | --- | --- | --- | --- | --- | --- |
|  |  | 1.06 | 2.09 | 3.04 | 0.94 | 1.94 | 2.86 |
| After reaction | Δabs | 0.174 | 0.278 | 0.326 | 0.066 | 0.007 | 0.069 |
|  | Δλ | 4 | 4 | 4 | 2 | 2 | 2 |
|  | % Δabs | 13.7 | 21.9 | 25.7 | 5.3 | 0.6 | 5.5 |
| After 1 week | Δabs | 0.143 | 0.348 | 0.442 | 0.063 | 0.031 | 0.254 |
|  | Δλ | 2 | 4 | 4 | 2 | 2 | 4 |
|  | % Δabs | 10.8 | 26.3 | 33.4 | −4.9 | 2.4 | 19.8 |

TABLE 8-continued comparison of ferulic acid and sinapic acid during one month as two potential aglycone anthocyanins' copigments

|  |  | Concentration ferulic (mM) | | | Concentration sinapic (mM) | | |
|---|---|---|---|---|---|---|---|
|  |  | 1.06 | 2.09 | 3.04 | 0.94 | 1.94 | 2.86 |
| After 2 weeks | Δabs | 0.143 | 0.348 | 0.442 | 0.084 | 0.111 | 0.391 |
|  | Δλ | 2 | 4 | 4 | 2 | 4 | 4 |
|  | % Δabs | 10.8 | 26.3 | 33.4 | −5.6 | −7.3 | 25.9 |
| After 1 month | Δabs | 0.143 | 0.348 | 0.442 | 0.236 | 0.321 | 0.102 |
|  | Δλ | 2 | 4 | 4 | 2 | 2 | 4 |
|  | % Δabs | 10.8 | 26.3 | 33.4 | 15.5 | 21.1 | 6.7 |

In order to study the effect of the ferulic acid and anthocyanins concentrations on the complex stability, the purified anthocyanins from previous process (0.09 mM) were mixed with ferulic acid at four different concentration levels, which resulted in four molar ratios of 1:22, 1:44, 1:88, and 1:176. The vials were kept at temperature of 40° C. for 60 min at natural pH of the extract (pH=3) and a sample without any cofactor was used as a control.

After reaching the equilibrium, absorption spectra of the samples were recorded using a UV-Visible spectrophotometer DR 3900 (Hatch, Düsseldorf, Germany), scanning a visible wavelength range from 400 to 700 nm. The stability of the co-pigmentation complex was measured by monitoring the hyperchromic effect and bathochromic shift of the co-pigmented samples and their corresponding control samples after reaction, 1 week, 2 weeks, and 1 month.

A hyperchromic effect was detected as an increase in the absorbance value at Amax and a bathochromic shift as a shift of the wavelength (nm) of Amax. For better interpretation of the data, the relative percentage of the hyperchromic and bathochromic shifts were calculated, referring to the control samples at the same conditions but without addition of the co-pigment.

Moreover, antioxidant activity of the different molar ratios co-pigmented samples was compared with their corresponding control samples after 1 month.

Figure 13A:
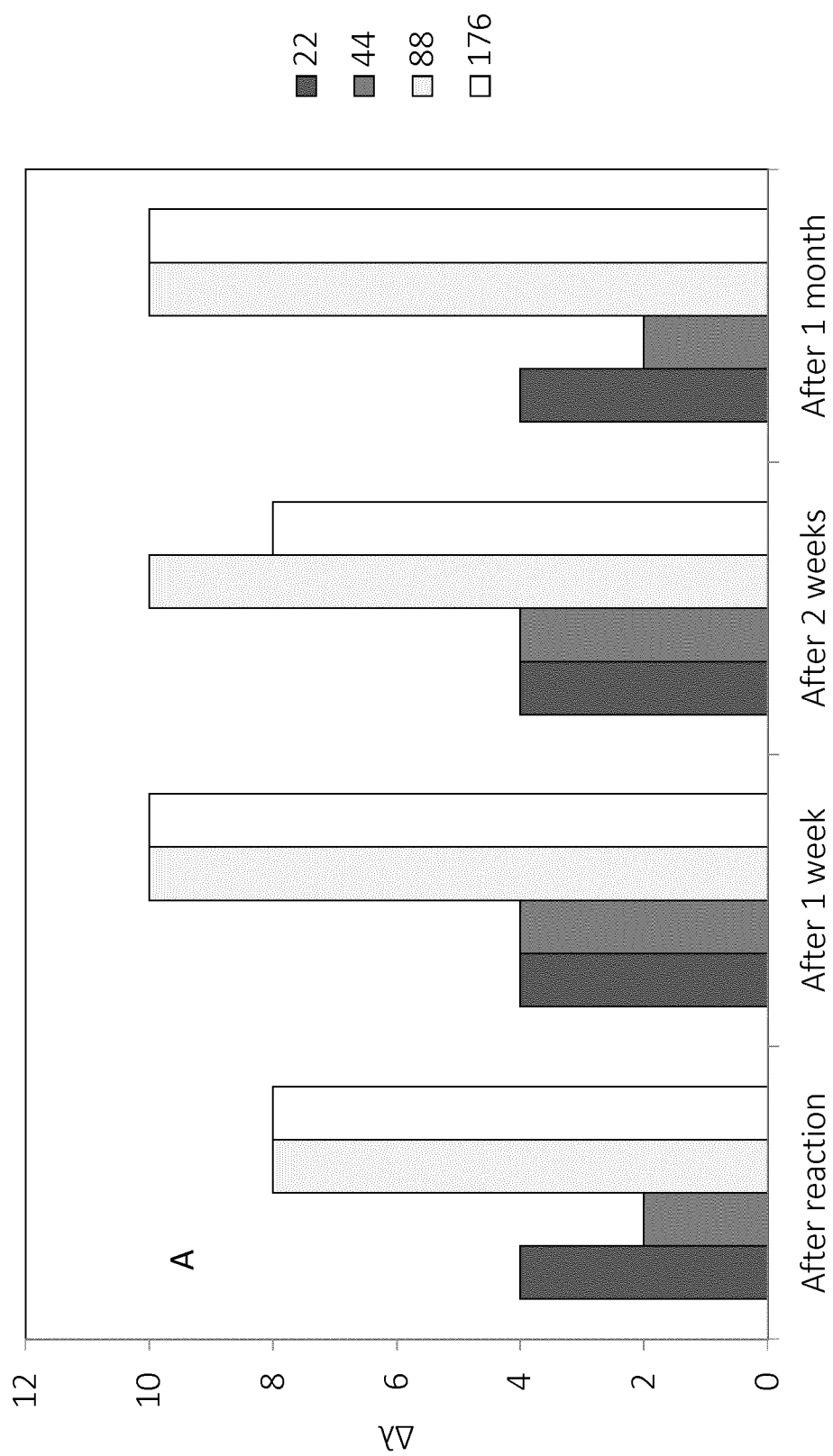
FIG. 13 shows the effect of different molar ratio of copigment:aglycone anthocyanin (22, 44, 88, and 176) on $\Delta\lambda$ (FIG. 13A), %$\Delta$abs (FIG. 13B), and $\Delta$I % (FIG. 13C) during 1 month storage at 5° C.; showing that the highest molar ratio of 176 is the best for preserving the aglycon anthocyanins.
Figure 13B:
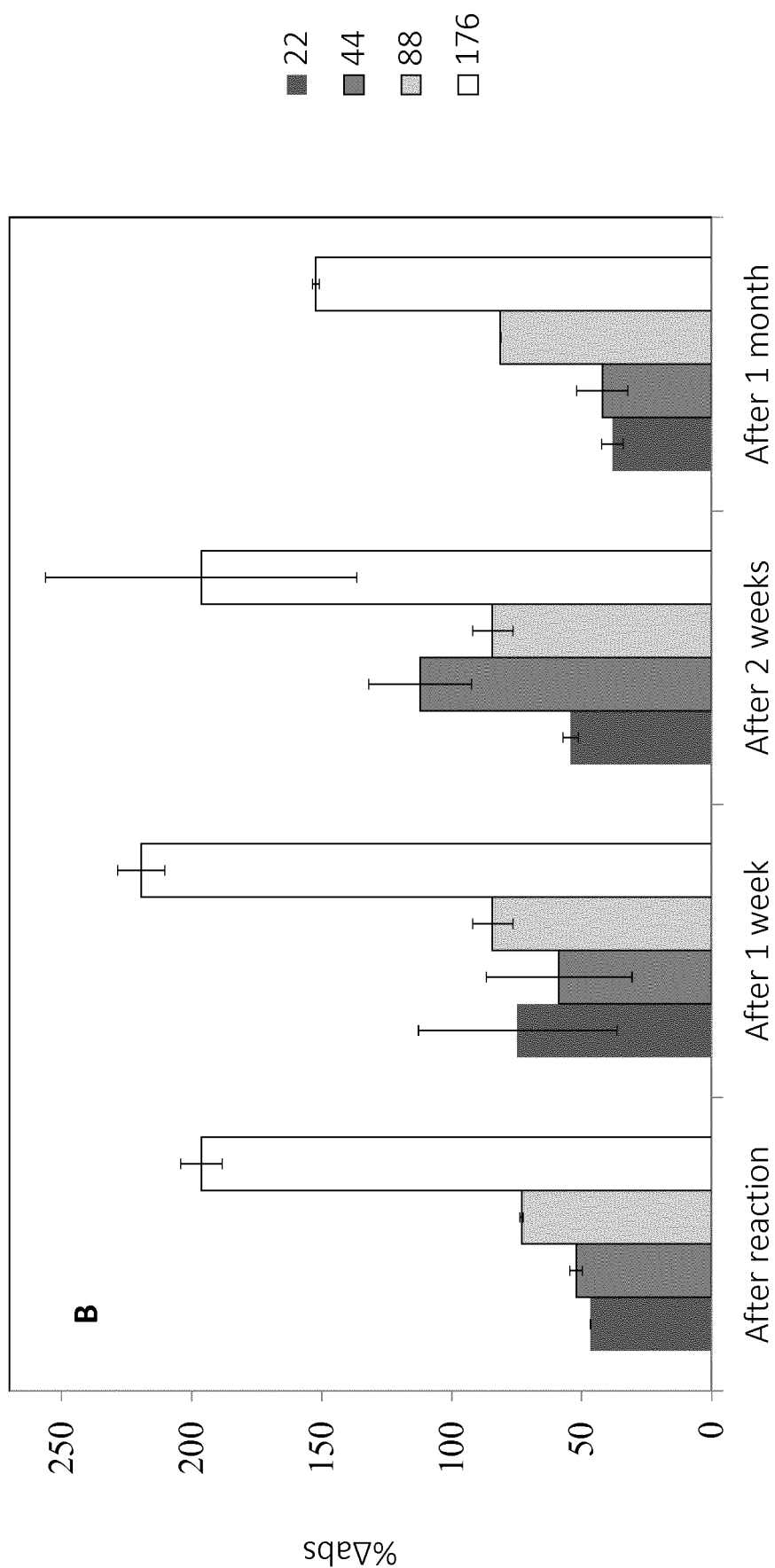
Figure 13C:
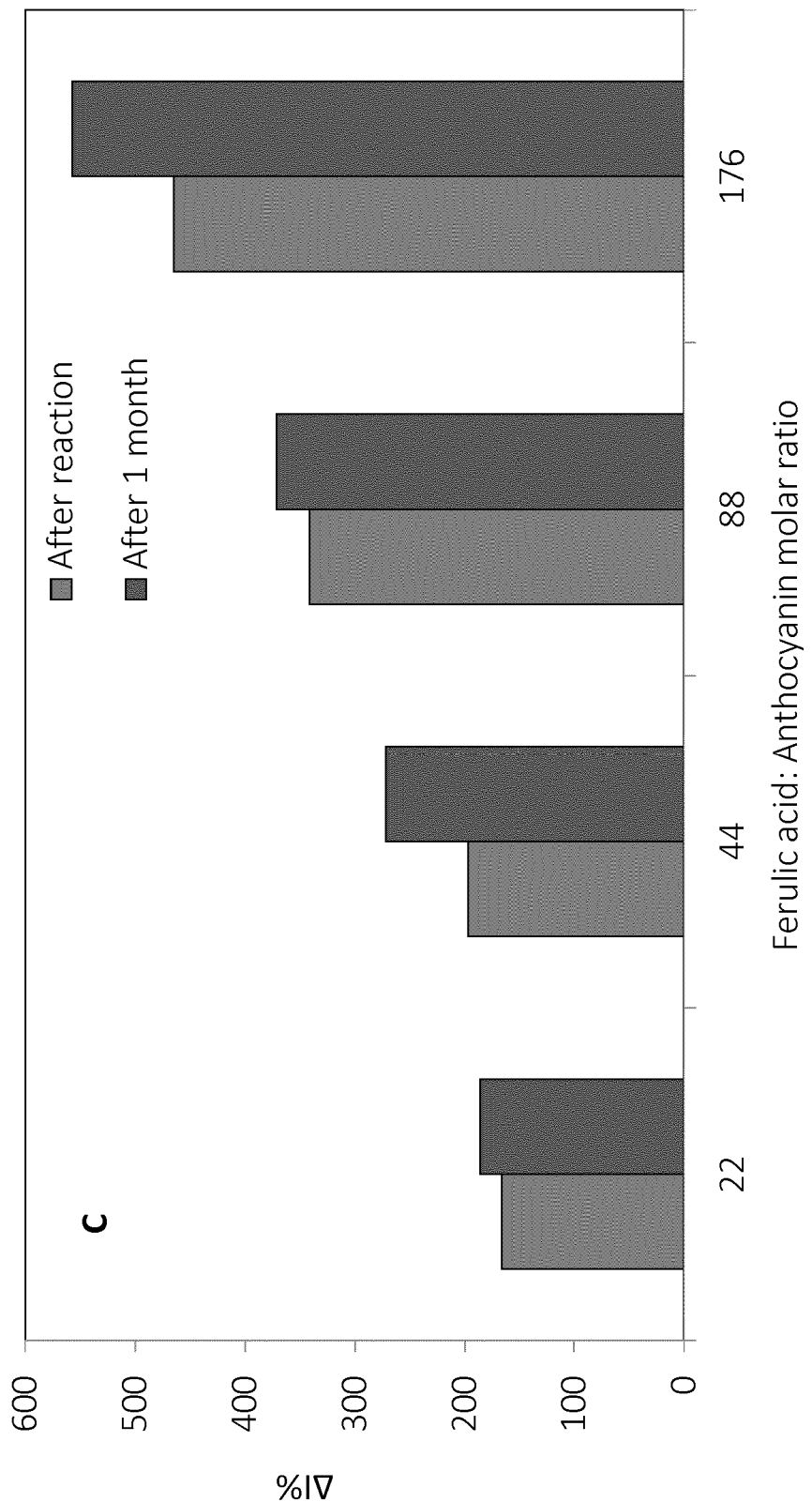

As shown in FIG. 13, during a month observation, a bathochromic shifts (Δλ) was the most at the two highest molar ratios (88 and 176), ranging from 8 to 10 (FIG. 13A). Moreover, the most increase of absorbance (%Δabs) was observed while adding the highest ferulic acid content (molar ratio of 176) which can be seen in FIG. 13B to be around 200%. However, the hyperchromic shif started to decrease to 150% after a month which it is still significantly higher than the control sample without cofactor. On the other hand, as shown in FIG. 13C, the ΔI % of the copigmented samples also increase after a month showing the preservation effect of cofactors during the storage period.

The observed hyperchromic effect and bathochromic shift are due to the increase in the electrons n-n system (chromophore) resulting from the formation of intermolecular association between anthocyanin and copigment.

Effect of Temperature and Light on Color Stability and Antioxidant Activity

Since Light and temperature are two factors that affect the colour stability of anthocyanins, the effects of white fluorescent light and temperature on the colour stability of anthocyanin, both natural and copigmented forms presented in Table 9. The anthocyanin: ferulic acid molar ratio of 1:176 was chosen to check the effect of temperature and light on the co-pigmented samples after 1 and 2 weeks. Some samples were kept in the fridge (5° C.) and others were kept at room temperature (20° C.) in order to check the effect of temperature. In addition, the samples at room temperature were divided into two groups, the first one protected from light while the other ones exposed constantly to white light. Stability of all samples were measured and compared with a control sample without the cofactor.

As seen in Table 9, the hypochromic and bathochromic shifts of the control samples (Ctrl.) were reduced after 2 weeks. The reduction of Δλ and %Δabs was observed to be the highest when the samples were kept in the room temperature and exposed to the light. Regarding the copigmented samples (Copig.), although Δλ and %Δabs have reduced slightly in the ende of the week two, it is worth mentioning that both LA and %Δabs had higher values compared to the Ctrl. samples after a specific time intervals. That proves the preservation effect of the cofactor in retarding the degradiation of aglycone anthocyanins.

TABLE 9 effect of copignnentation on stability of aglycone anthocynins kept in dark and 5 C; room temperature, and exposed to light at room temperature during 2 weeks

|  |  | Ctrl. (5° C.) | Ctrl. Room T | Crtl. Light + room T | Copig. (5° C.) | Copig. room T | Copig light + room T |
|---|---|---|---|---|---|---|---|
| After reaction | Δabs | 0 | −0.013 | −0.085 | 0.805 | 0.904 | 0.955 |
|  | Δλ | 0 | 0 | 0 | 14 | 12 | 12 |
|  | % Δabs | 0.0 | −2.1 | −14.7 | 56.8 | 64.5 | 67.4 |
| After 1 week | Δabs | −0.002 | −0.044 | −0.140 | 1.165 | 1.087 | 1.217 |
|  | Δλ | 0 | 0 | 0 | 12 | 10 | 10 |
|  | % Δabs | −0.3 | −7.6 | −23.9 | 199.7 | 201.7 | 274.1 |
| After 2 weeks | Δabs | −0.022 | −0.079 | −0.200 | 0.880 | 0.756 | 0.734 |
|  | Δλ | 0 | 0 | 0 | 10 | 8 | 8 |
|  | % Δabs | −3.8 | −13.6 | −34.2 | 150.8 | 150.0 | 191.1 |

The invention claimed is:

1. Method for obtaining natural colorants from materials of plant origin, comprising the following steps:

(a) adding pomace from said materials of plant origin and a aqueous buffer solution into a mixing device (b) mixing said pomace from said materials and aqueous buffer solution, followed by (c) blending the mixed pomace obtained in step (b) in a blending device thereby obtaining a comminute homogenized slurry, followed by (d) adding one or more hydroxycinnamic acid(s) into the slurry obtained in step (c), and (e) adding one or more one or more hydrolytic enzyme(s) to the slurry of step (c) or (d), and (f) adding one or more green solvent(s) to the slurry of step (c), (d) or (e) (g) subjecting the resulting mixture obtained in step (f) to ultrafiltration in a ultrafiltration unit thereby obtaining a permeate rich in natural colorants wherein the pH in all steps (a)-(g) is kept at or below 3 and wherein the temperature in all steps (a)-(g) is kept at or below 50° C.

2. Method according to claim 1, wherein steps (a)-(c)are carried out in a batch process.

3. Method according to claim 1, wherein steps (d)-(f) are carried out in a reactor vessel, an enzyme reaction tank, a storage tank or a fermenter.

4. Method according to claim 1, wherein the comminute homogenized slurry obtained in step (c) is transferred to a reactor vessel by a fed-batch process.

5. Method according to claim 1, wherein the one or more hydroxycinnamic acid(s) is/are selected from a group consisting of natural phenolic acids, ferulic acid, α-cyano-4-hydroxycinnamic acid, caffeic acid, cichoric acid, cinnamic acid, chlorogenic acid, diferulic acids, coumaric acid, coumarin, ferulic acid, sinapic acid, benzoic acid and gallic acid.

6. Method according to claim 1, wherein the one or more hydrolytic enzyme(s) is/are selected from a group consisting of ligninases, lignin peroxidases, pectolytic enzymes, pectinases, glucanase, arabinose, galactanase, rhamno-galcturonase, laccases, cellulases and hemi-cellulases.

7. Method according to claim 1, where the addition of green solvent in step (f) results in green solvent: slurry ratio of 30-50:1 (w/w).

8. Method according to claim 1, wherein the permeate rich in natural colorants obtained in step (g) comprises antioxidant-containing pigments selected from a water-soluble group of compounds consisting of anthocyanin, polyphenols, tannic acid, ellagitannin, catechin, phenol, flavonoid and flavonol.

9. Method according to claim 1, wherein the materials of plant origin are selected from the group consisting of fruits, berries, black berries, cherries, red currants, apple, aronia, elderberry, raspberry, strawberry, black chokeberry (Aronia Melanocarpa), cowberry, bilberry, and black elderberry.

10. Method according to claim 1, wherein the pomace and buffer solution of step (a) are in a ratio of 1:50 w/w.

11. Method according to claim 1, wherein the ultrafiltration unit of step (g) comprises a molecular cut-off of 20 kDa-50 kDa.

12. Method according to claim 1, wherein the only green solvent used in step (f) is water.

13. Method according to claim 1, wherein the permeate rich in natural colorants obtained in step (g) are concentrated by vacuum drying.

14. Method according to claim 1, wherein the permeate rich in natural colorants obtained in step (g) is subjected to a diafiltration treatment in a nanofiltration unit.

15. Method according to claim 14, wherein the nanofiltration unit comprises a nanofiltration-membrane having pore size between 600 Da-1 kDa.

\* \* \* \* \*